(12) United States Patent
Lü et al.

(10) Patent No.: US 8,642,545 B2
(45) Date of Patent: Feb. 4, 2014

(54) ERYTHROPOIETIN MIMETIC PEPTIDE DERIVATIVE AND ITS PHARMACEUTICAL SALTS, THE PREPARATION AND USES THEREOF

(75) Inventors: Aifeng Lü, Jiangsu (CN); Changan Sun, Jiangsu (CN); Tao Jiang, Jiangsu (CN); Wentao Wu, Jiangsu (CN); Yali Wang, Markham (CA)

(73) Assignee: Jiangsu Hansoh Pharmaceutical Co., Ltd, Jiangsu (CN)

(*) Notice: Subject to any disclaimer, the term of this patent is extended or adjusted under 35 U.S.C. 154(b) by 379 days.

(21) Appl. No.: 12/747,818

(22) PCT Filed: Nov. 24, 2008

(86) PCT No.: PCT/CN2008/001909
§ 371 (c)(1),
(2), (4) Date: Jun. 11, 2010

(87) PCT Pub. No.: WO2009/079910
PCT Pub. Date: Jul. 2, 2009

(65) Prior Publication Data
US 2010/0323949 A1 Dec. 23, 2010

(30) Foreign Application Priority Data
Dec. 12, 2007 (CN) .......................... 2007 1 0198751

(51) Int. Cl.
*C07K 14/505* (2006.01)

(52) U.S. Cl.
USPC .......................................... 514/7.7; 530/326

(58) Field of Classification Search
USPC .......................................... 530/326; 514/7.7
See application file for complete search history.

(56) References Cited

U.S. PATENT DOCUMENTS

| | | | |
|---|---|---|---|
| 6,077,939 A | 6/2000 | Wei et al. | |
| 7,084,245 B2 | 8/2006 | Holmes et al. | |
| 7,414,105 B2 | 8/2008 | Holmes et al. | |
| 7,528,104 B2 | 5/2009 | Holmes et al. | |
| 7,855,175 B2 | 12/2010 | Holmes et al. | |
| 8,304,391 B2 | 11/2012 | Holmes et al. | |
| 2005/0107297 A1 | 5/2005 | Holmes et al. | |
| 2005/0137329 A1* | 6/2005 | Holmes et al. | 525/54.1 |
| 2006/0040858 A1 | 2/2006 | Holmes et al. | |
| 2007/0027074 A1 | 2/2007 | Holmes et al. | |
| 2009/0048166 A1 | 2/2009 | Holmes et al. | |
| 2009/0227508 A1 | 9/2009 | Holmes et al. | |
| 2011/0245176 A1 | 10/2011 | Holmes et al. | |

FOREIGN PATENT DOCUMENTS

| WO | WO 90/08822 | 8/1990 |
|---|---|---|
| WO | WO 2006/060148 A2 | 6/2006 |
| WO | WO 2006/062685 A2 | 6/2006 |

OTHER PUBLICATIONS

Sasaki, Hiroshi et al., *Carbohydrate Structure of Erythropoietin Expressed in Chinese Hamster Ovary Cells by a Human Erythropoientin cDNA*, The Journal of Biological Chemistry, Sep. 1987, pp. 12059-12076, vol. 262, No. 25, Issue of Sep. 5, U.S.A.
Danna, Robert P., et al, *Erythropoietin Therapy for the Anemia Associated with AIDS and AIDS Therapy and Cancer*, Edited by Garnick, M.S., *Erythropoietin in Clinical Applications—An International Perspective*, Marcel Dekker, 1990, The R.W. Johnson Pharmaceutical Research Institute, pp. 301-324, Raritan, New Jersey.
Egrie, J. C., et al. *Characterization and Biological Effects of Recombinant Human Erythropoietin*, Immunobiol, Fol. 172, pp. 213-214 (1986), Amgen, Thousand Oaks, CA, U.S.A.
Abstract of CN 1338463 A, issued Mar. 2002.
Abstract of CN 1680449 A, issued Oct. 2005.
International Search Report for corresponding International Application No. PCT/CN2008/001909, 12 pages (Feb. 26, 2009).
Johnson, Dana L., et al., "Amino-terminal Dimerization of an Erythropoietin Mimetic Peptide Results in Increased Erythropoietic Activity," *Chemistry & Biology*, 4(12):939-950 (1997).
Sawyer, T. Stephen, et al., "Identification of the Receptor for Erthropoietin by Cross-Linking to Friend Virus-Infected Erythroid Cells," *Proc. Natl. Acad. Sci. USA*, 84:3690-3694 (Jun. 1987).

* cited by examiner

*Primary Examiner* — David Lukton
(74) *Attorney, Agent, or Firm* — Brinks Gilson & Lione; Ryan L. Marshall

(57) ABSTRACT

What is provided is EPO mimetic peptide derivatives defined as formula (I) and their pharmaceutical salts, the preparation thereof, wherein $R^1$, $R^2$, $R^3$, $R^4$, $R^5$, $n_1$, $n_2$ are defined as described in description. A composition comprising of an EPO mimetic peptide derivative defined as formula (I) and its pharmaceutical salt. The uses of the derivatives and their pharmaceutical salts, as well as the uses of the compositions described above in treatment of diseases characterized by a deficiency of EPO or a low or defective red blood cell population.

$$R^1-R^2-(CH_2)_{n1}-R^3-(CH_2)_{n2}-R^4-R^5 \quad (I)$$

34 Claims, 1 Drawing Sheet

SEQUENCE LISTING

<160> NUMBER OF SEQ ID NOS: 30

<210> SEQ ID NO 1
<211> LENGTH: 22
<212> TYPE: PRT
<213> ORGANISM: Artificial Sequence

```
<220> FEATURE:
<223> OTHER INFORMATION: chemically synthesized
<220> FEATURE:
<221> NAME/KEY: Acetylation
<222> LOCATION: (1)..(1)
<220> FEATURE:
<221> NAME/KEY: Amidation
<222> LOCATION: (6)..(15)

<400> SEQUENCE: 1

Gly Gly Leu Tyr Ala Asp His Tyr Gly Pro Ile Thr Trp Val Lys Gln
1               5                   10                  15

Pro Leu Arg Gly Gly Lys
            20

<210> SEQ ID NO 2
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: Acetylation
<222> LOCATION: (1)..(1)
<220> FEATURE:
<221> NAME/KEY: Amidation
<222> LOCATION: (6)..(15)
<220> FEATURE:
<221> NAME/KEY: MISC_FEATURE
<222> LOCATION: (15)..(15)
<223> OTHER INFORMATION: Xaa=Orn

<400> SEQUENCE: 2

Gly Gly Leu Tyr Ala Asp His Tyr Gly Pro Ile Thr Trp Val Xaa Gln
1               5                   10                  15

Pro Leu Arg Gly Gly Lys
            20

<210> SEQ ID NO 3
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: amidation
<222> LOCATION: (6)..(15)

<400> SEQUENCE: 3

Gly Gly Leu Tyr Ala Lys His Tyr Gly Pro Ile Thr Trp Val Asp Gln
1               5                   10                  15

Pro Leu Arg Gly Gly Lys
            20

<210> SEQ ID NO 4
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: amidation
<222> LOCATION: (6)..(15)
<220> FEATURE:
<221> NAME/KEY: MISC_FEATURE
```

```
<222> LOCATION: (6)..(6)
<223> OTHER INFORMATION: Xaa=Orn

<400> SEQUENCE: 4

Gly Gly Leu Tyr Ala Xaa His Tyr Gly Pro Ile Thr Trp Val Asp Gln
1               5                   10                  15

Pro Leu Arg Gly Gly Lys
            20

<210> SEQ ID NO 5
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: Disulfid
<222> LOCATION: (6)..(15)
<220> FEATURE:
<221> NAME/KEY: MISC_FEATURE
<222> LOCATION: (21)..(21)
<223> OTHER INFORMATION: Xaa=bAla

<400> SEQUENCE: 5

Gly Gly Thr Tyr Ser Cys His Phe Gly Pro Leu Thr Trp Val Cys Arg
1               5                   10                  15

Pro Gln Arg Gly Xaa Lys
            20

<210> SEQ ID NO 6
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: disulfid
<222> LOCATION: (6)..(15)
<220> FEATURE:
<221> NAME/KEY: MISC_FEATURE
<222> LOCATION: (7)..(21)
<223> OTHER INFORMATION: No. 7 Xaa = Nle; No. 21 Xaa = bAla

<400> SEQUENCE: 6

Gly Gly Thr Tyr Ser Cys Xaa Phe Gly Pro Leu Thr Trp Val Cys Arg
1               5                   10                  15

Pro Gln Arg Gly Xaa Lys
            20

<210> SEQ ID NO 7
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: disulfid
<222> LOCATION: (6)..(15)
<220> FEATURE:
<221> NAME/KEY: MISC_FEATURE
<222> LOCATION: (21)..(21)
<223> OTHER INFORMATION: Xaa=bAla
```

-continued

<400> SEQUENCE: 7

Gly Gly Thr Tyr Ser Cys His Phe Gly Ser Leu Thr Trp Val Cys Arg
1               5                   10                  15

Pro Gln Arg Gly Xaa Lys
            20

<210> SEQ ID NO 8
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: disulfid
<222> LOCATION: (6)..(15)
<220> FEATURE:
<221> NAME/KEY: MISC_FEATURE
<222> LOCATION: (21)..(21)
<223> OTHER INFORMATION: Xaa=bAla

<400> SEQUENCE: 8

Gly Gly Thr Tyr Ser Cys His Phe Gly Ala Leu Thr Trp Val Cys Arg
1               5                   10                  15

Pro Gln Arg Gly Xaa Lys
            20

<210> SEQ ID NO 9
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: amidation
<222> LOCATION: (6)..(15)

<400> SEQUENCE: 9

Gly Gly Leu Tyr Ala Asp His Tyr Gly Pro Met Thr Trp Val Lys Gln
1               5                   10                  15

Pro Leu Arg Gly Gly Lys
            20

<210> SEQ ID NO 10
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: amidation
<222> LOCATION: (6)..(15)
<220> FEATURE:
<221> NAME/KEY: MISC_FEATURE
<222> LOCATION: (15)..(15)
<223> OTHER INFORMATION: Xaa=Orn

<400> SEQUENCE: 10

Gly Gly Leu Tyr Ala Asp His Tyr Gly Pro Met Thr Trp Val Xaa Gln
1               5                   10                  15

Pro Leu Arg Gly Gly Lys
            20

<210> SEQ ID NO 11
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: amidation
<222> LOCATION: (6)..(15)
<220> FEATURE:
<221> NAME/KEY: MISC_FEATURE
<222> LOCATION: (6)..(6)
<223> OTHER INFORMATION: Xaa=Orn

<400> SEQUENCE: 11

Gly Gly Leu Tyr Ala Xaa His Tyr Gly Pro Met Thr Trp Val Asp Gln
1               5                   10                  15

Pro Leu Arg Gly Gly Lys
            20

<210> SEQ ID NO 12
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: amidation
<222> LOCATION: (6)..(15)
<220> FEATURE:
<221> NAME/KEY: MISC_FEATURE
<222> LOCATION: (21)..(21)
<223> OTHER INFORMATION: Xaa=bAla

<400> SEQUENCE: 12

Gly Gly Thr Tyr Ser Lys His Phe Gly Pro Met Thr Trp Val Asp Arg
1               5                   10                  15

Pro Gln Arg Gly Xaa Lys
            20

<210> SEQ ID NO 13
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: disulfid
<222> LOCATION: (6)..(15)
<220> FEATURE:
<221> NAME/KEY: MISC_FEATURE
<222> LOCATION: (21)..(21)
<223> OTHER INFORMATION: Xaa=bAla

<400> SEQUENCE: 13

Gly Gly Thr Tyr Ser Cys His Phe Gly Pro Ile Thr Trp Val Cys Arg
1               5                   10                  15

Pro Gln Arg Gly Xaa Lys
            20

```
<210> SEQ ID NO 14
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: disulfid
<222> LOCATION: (6)..(15)
<220> FEATURE:
<221> NAME/KEY: MISC_FEATURE
<222> LOCATION: (15)..(21)
<223> OTHER INFORMATION: No. 15 Xaa = Homocysteine; No. 21 Xaa = bAla

<400> SEQUENCE: 14

Gly Gly Thr Tyr Ser Cys His Phe Gly Pro Met Thr Trp Val Xaa Arg
1               5                   10                  15

Pro Gln Arg Gly Xaa Lys
            20

<210> SEQ ID NO 15
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: disulfid
<222> LOCATION: (6)..(15)
<220> FEATURE:
<221> NAME/KEY: MISC_FEATURE
<222> LOCATION: (15)..(21)
<223> OTHER INFORMATION: No. 15 Xaa = Homocysteine; No. 21 Xaa = bAla

<400> SEQUENCE: 15

Gly Gly Thr Tyr Ser Cys His Phe Gly Pro Ile Thr Trp Val Xaa Arg
1               5                   10                  15

Pro Gln Arg Gly Xaa Lys
            20

<210> SEQ ID NO 16
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: disulfid
<222> LOCATION: (6)..(15)
<220> FEATURE:
<221> NAME/KEY: MISC_FEATURE
<222> LOCATION: (7)..(15)
<223> OTHER INFORMATION: No. 7 Xaa = Nle; No. 15 Xaa = Homocysteine
<220> FEATURE:
<221> NAME/KEY: misc_feature
<222> LOCATION: (21)..(21)
<223> OTHER INFORMATION: No. 21 Xaa = bAla

<400> SEQUENCE: 16

Gly Gly Thr Tyr Ser Cys Xaa Phe Gly Pro Met Thr Trp Val Xaa Arg
1               5                   10                  15
```

```
Pro Gln Arg Gly Xaa Lys
            20

<210> SEQ ID NO 17
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: disulfid
<222> LOCATION: (6)..(15)
<220> FEATURE:
<221> NAME/KEY: MISC_FEATURE
<222> LOCATION: (7)..(21)
<223> OTHER INFORMATION: No. 7 Xaa = Nle; No. 21 Xaa = bAla

<400> SEQUENCE: 17

Gly Gly Thr Tyr Ser Cys Xaa Phe Gly Pro Ile Thr Trp Val Cys Arg
1               5                  10                  15

Pro Gln Arg Gly Xaa Lys
            20

<210> SEQ ID NO 18
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: disulfid
<222> LOCATION: (6)..(15)
<220> FEATURE:
<221> NAME/KEY: MISC_FEATURE
<222> LOCATION: (21)..(21)
<223> OTHER INFORMATION: Xaa=bAla

<400> SEQUENCE: 18

Gly Gly Thr Tyr Ser Cys His Phe Gly Pro Leu Thr Trp Val Cys Arg
1               5                  10                  15

Pro Gln Arg Gly Xaa Lys
            20

<210> SEQ ID NO 19
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: disulfid
<222> LOCATION: (6)..(15)
<220> FEATURE:
<221> NAME/KEY: MISC_FEATURE
<222> LOCATION: (21)..(21)
<223> OTHER INFORMATION: Xaa=bAla

<400> SEQUENCE: 19

Gly Gly Thr Tyr Ser Cys His Phe Gly Ser Ile Thr Trp Val Cys Arg
1               5                  10                  15

Pro Gln Arg Gly Xaa Lys
            20
```

```
<210> SEQ ID NO 20
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: amidation
<222> LOCATION: (6)..(15)
<220> FEATURE:
<221> NAME/KEY: MISC_FEATURE
<222> LOCATION: (21)..(21)
<223> OTHER INFORMATION: Xaa=bAla

<400> SEQUENCE: 20

Gly Gly Thr Tyr Ser Lys His Phe Gly Ser Met Thr Trp Val Glu Arg
1               5                   10                  15

Pro Gln Arg Gly Xaa Lys
            20

<210> SEQ ID NO 21
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: disulfid
<222> LOCATION: (6)..(15)

<400> SEQUENCE: 21

Gly Gly Thr Tyr Arg Cys Ser Met Gly Pro Met Thr Trp Val Cys Leu
1               5                   10                  15

Pro Met Ala Gly Gly Lys
            20

<210> SEQ ID NO 22
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: disulfid
<222> LOCATION: (6)..(15)

<400> SEQUENCE: 22

Gly Gly Thr Tyr Arg Cys Ser Met Gly Pro Leu Thr Trp Val Cys Leu
1               5                   10                  15

Pro Met Ala Gly Gly Lys
            20

<210> SEQ ID NO 23
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
```

```
<222> LOCATION: (1)..(1)
<220> FEATURE:
<221> NAME/KEY: disulfid
<222> LOCATION: (6)..(15)
<220> FEATURE:
<221> NAME/KEY: MISC_FEATURE
<222> LOCATION: (21)..(21)
<223> OTHER INFORMATION: Xaa=bAla

<400> SEQUENCE: 23

Gly Gly Thr Tyr Ser Cys His Phe Gly Ala Met Thr Trp Val Cys Arg
1               5                   10                  15

Pro Gln Arg Gly Xaa Lys
            20

<210> SEQ ID NO 24
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: disulfid
<222> LOCATION: (6)..(15)
<220> FEATURE:
<221> NAME/KEY: MISC_FEATURE
<222> LOCATION: (21)..(21)
<223> OTHER INFORMATION: Xaa=bAla

<400> SEQUENCE: 24

Gly Gly Thr Tyr Ser Cys His Phe Gly Ala Ile Thr Trp Val Cys Arg
1               5                   10                  15

Pro Gln Arg Gly Xaa Lys
            20

<210> SEQ ID NO 25
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: disulfid
<222> LOCATION: (6)..(15)
<220> FEATURE:
<221> NAME/KEY: MISC_FEATURE
<222> LOCATION: (21)..(21)
<223> OTHER INFORMATION: Xaa=bAla

<400> SEQUENCE: 25

Gly Gly Thr Tyr Ser Cys His Phe Gly Pro Ile Thr Trp Val Cys Arg
1               5                   10                  15

Pro Gln Arg Gly Xaa Lys
            20

<210> SEQ ID NO 26
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
```

```
<221> NAME/KEY: disulfid
<222> LOCATION: (6)..(15)
<220> FEATURE:
<221> NAME/KEY: MISC_FEATURE
<222> LOCATION: (21)..(21)
<223> OTHER INFORMATION: Xaa=bAla

<400> SEQUENCE: 26

Gly Gly Thr Tyr Ser Cys His Phe Gly Pro Leu Thr Trp Val Cys Arg
1               5                   10                  15

Pro Gln Arg Gly Xaa Lys
            20

<210> SEQ ID NO 27
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: Acetylation
<222> LOCATION: (1)..(1)
<220> FEATURE:
<221> NAME/KEY: disulfid
<222> LOCATION: (6)..(15)

<400> SEQUENCE: 27

Gly Gly Met Tyr Ser Cys Arg Met Gly Pro Met Thr Trp Val Cys Gly
1               5                   10                  15

Pro Ser Arg Gly Gly Lys
            20

<210> SEQ ID NO 28
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: disulfid
<222> LOCATION: (6)..(15)

<400> SEQUENCE: 28

Gly Gly Met Tyr Ser Cys Arg Met Gly Pro Leu Thr Trp Val Cys Gly
1               5                   10                  15

Pro Ser Arg Gly Gly Lys
            20

<210> SEQ ID NO 29
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: disulfid
<222> LOCATION: (6)..(15)
<220> FEATURE:
<221> NAME/KEY: MISC_FEATURE
<222> LOCATION: (15)..(21)
<223> OTHER INFORMATION: No. 15 Xaa = Homocysteine; No. 21 Xaa = bAla

<400> SEQUENCE: 29

Gly Gly Thr Tyr Ser Cys His Phe Gly Pro Leu Thr Trp Val Xaa Arg
```

```
1               5               10              15
Pro Gln Arg Gly Xaa Lys
                20

<210> SEQ ID NO 30
<211> LENGTH: 22
<212> TYPE: PRT
<213> ORGANISM: Artificial Sequence
<220> FEATURE:
<223> OTHER INFORMATION: chemically synthesized
<220> FEATURE:
<221> NAME/KEY: acetylation
<222> LOCATION: (1)..(1)
<220> FEATURE:
<221> NAME/KEY: disulfid
<222> LOCATION: (6)..(15)
<220> FEATURE:
<221> NAME/KEY: MISC_FEATURE
<222> LOCATION: (6)..(21)
<223> OTHER INFORMATION: No. 6 Xaa = Homocysteine; No. 21 Xaa = bAla

<400> SEQUENCE: 30

Gly Gly Thr Tyr Ser Xaa His Phe Gly Pro Leu Thr Trp Val Cys Arg
1               5               10              15

Pro Gln Arg Gly Xaa Lys
                20
```

ERYTHROPOIETIN MIMETIC PEPTIDE DERIVATIVE AND ITS PHARMACEUTICAL SALTS, THE PREPARATION AND USES THEREOF

The present application is the national phase application of PCT Application No. PCT/CN2008/001909, filed Nov. 24, 2008, which claims priority to Chinese Patent Application No. 200710198751.9, filed Dec. 12, 2007, the entireties of all of which are hereby incorporated by references.

The contents of the sequence listing are incorporated into the present disclosure by reference.

The contents of the sequence listing "14271-9_Sequence_Listing_ST25" are incorporated into the present disclosure by reference. The sequence listing was created on Aug. 24, 2010 and has a size of 13.8 k.

FIELD

The present invention relates to erythropoietin (EPO) mimetic peptide derivatives and their pharmaceutical salts that bind to the EPO receptor and activate the EPO receptor, or have the agonistic effect of EPO. Specifically, the present invention relates to EPO mimetic peptide derivatives modified by active methoxy polyethylene glycol and methods for preparing such derivatives. The present invention also relates to treatment of disorders characterized by low levels of EPO or insufficient or defective red blood cell population, using said mimetic peptide derivatives and their pharmaceutical salts.

BACKGROUND

EPO is a glycoprotein hormone with a molecular weight of about 34 kD. EPO in the plasma is composed of 165 amino acids with a high degree of glycosylation, wherein the major component of glycosyl is sialic acid. Based on carbohydrate content, naturally occurring EPO is divided into two types, namely α and β-type, wherein α-type contains 34% carbohydrate and β-type contains 26% carbohydrate. These two types have the same biological characteristics, antigenicity and clinical effect. The human EPO gene is located on chromosome 7 long-Area 22. Its cDNA was successfully cloned in 1985, and recombinant human EPO (rHuEPO) has been largely produced using gene recombinant technology and widely used in the clinic. EPO has been biosynthesized using recombinant DNA technology (Egrie, J. C., Strickland, T W, Lane, J. etc. (986), Immunobiology, 72: 213-224). The biosynthesized EPO is the expression product of cloned human EPO gene in Chinese hamster ovary cells (CHO cells). Naturally occurring human EPO is firstly translated into polypeptide chains containing 166 amino acids with position 166 being arginine. In the post-translational modifications, arginine on position 166 is degraded using hydroxyl peptidase. The molecular weight of human EPO without glycosyl is 18236 Da. In the intact EPO molecule, glycosylation accounts for about 40% of the total molecular weight (J. Biol. Chem., 262: 12059).

EPO is the first cytokine applied in clinic and by far the best known hemoglobin-increasing drug with unique and safe effects. It has certain therapeutic effects on renal anemia, aplastic anemia, multiple myeloma, and paroxysmal nocturnal hematuria. In addition, the application of EPO can reduce the requirement of blood transfusion in surgery, and to some extent cure anemia caused by malignant tumor, chemotherapy and rheumatoid arthritis. Since EPO is primarily generated by renal tubular endothelial cells, anemia caused by renal disease is the first indication of EPO. The curative efficacy of EPO on renal anemia is almost 100%, but EPO does not improve renal function. Treatment with EPO is safe, effective and suitable for long-term treatment. In addition, it addresses the problem of shortage of blood supply. On the global market for biotechnology drugs in 2006, EPO recombinant drugs accounted for 11.9 billion U.S. dollars. There exists a huge market capacity.

As early as 1989, recombinant human EPO (EPOGEN®) was approved by U.S. FDA for the treatment of renal anemia, but it entered Chinese market only in 1992. The annual morbidity of chronic nephritis is about 0.25% in China, of which a considerable proportion of patients will eventually develop renal failure. The number of patients with renal anemia is about 500-600 thousands each year. According to conservative estimates of consumption of the drug in the renal anemia, together with consumption in other cancer-related anemia, the domestic market capacity is about 1.2-1.6 billion CNY or even more (calculated with the current price being 30-40 CNY/dose, the average weight of patients being 50 Kg). From the late 1990s, EPO has been ranked among the best-selling drugs in China's major cities. The cost of EPO is 62.13 million CNY in sample hospitals of major cities all over China in 2003, ranking number 56. The cost of EPO in sample hospitals of major cities all over China increased to 80.49 million CNY in 2004, with an annual increase of 30%.

As an endogenous hormone acting on the marrow hematopoietic cells to promote proliferation, differentiation and ultimate mature of erythroid progenitor cells, EPO plays an important role in regulating oxygen status of the body. In the early embryo stage, EPO is generated by the liver, then the production site of EPO gradually shifts to the kidney. EPO is mainly secreted by renal tubular interstitial cells after birth.

During induction of red progenitor cell differentiation by EPO, the globulin synthesis is induced, which allows cells to recruit more hemoglobin with functions of heme synthesis. The hemoglobin can combine with oxygen in mature red blood cells. Therefore, red blood cell and hemoglobin play an important role in supplying oxygen to the body. This process is initiated by the interaction between EPO and surface receptors of red progenitor cells.

When the body is in a healthy state, the tissue may obtain enough oxygen from already existing red blood cells. At this time the body's EPO concentration is very low. This low but normal concentration of EPO is sufficient to stimulate the generation of red blood cells, which is normally lost during aging.

When the level of oxygen transported by red blood cells in the circulation system is reduced and hypoxia appears, the amount of EPO in the body will increase. The body's hypoxic state may be caused by the following reasons: excessive exposure to radiation, reduced oxygen intake due to high latitude or long term coma, various types of anemia and so on. As a response to hypoxic stress of the body, a higher level of EPO can stimulate the differentiation of red progenitor cell to enhance its ability to produce red blood cells. When the number of red blood cells in the body exceeds the need of the normal tissue, the level of EPO in the circulation system is reduced. Because EPO plays a crucial role for the formation of red blood cells, this hormone has a broad potential for the treatment and diagnosis of blood diseases characterized by low generation of and/or defective red blood cells. Recent studies provide the basis for predicting the effect of EPO therapy in a variety of diseases, disorders, and hematological abnormalities. Applications of EPO include: the use of EPO in the treatment of anemia in patients with chronic renal failure (CRF), and administration of EPO to patients with AIDS and receiving chemotherapy (Danna, R. P., Rudnick, S. A., Abels, R I: edited by M B, Garnick, EPO in Clinical Applications—An International Perspective. Marcel Dekker; 1990: p 301-324).

Part of the biological effects of EPO can be regulated by interaction with surface receptors on the cell membrane. Previously, when studying the binding of EPO protein to cell surface using immature red blood cells isolated from mice spleen, it is found that this protein is composed of two polypeptides, having molecular weights of approximately 85,000~100,000 KD (see Sawyer, et al. (1987) Proc. Natl. Acad. Sci. USA 84:3690-3694 for a more detailed description). The number of binding sites of EPO has also been calculated. Each cell membrane contains about 800 to 1000 sites. In these binding sites, about 300 binding sites have a $K_d$ value of 90 pM. The binding of the remaining binding sites is weak, being about 570 pM. Some studies have shown that, from the response to EPO of red blood cells from the spleen of mice infected with the Friend virus anemia strain, about 400 binding sites are identified, wherein some have a high Kd of 100 pM and some have a low Kd of 800 pM.

Subsequent work has shown that the two types of EPO receptor are transcribed from a single gene. This gene has been cloned now. For example, the DNA sequences and peptide encoding sequences of the mouse and human EPO receptor have been described in WO90/08822. Current models show that binding of EPO to EPO receptor leads to activation and dimerization of two EPO receptors. This dimerization further leads to the initiation of signal transduction.

The cloned gene of EPO can be used to find agonists and antagonists of these important receptors. Peptides that interact to some extent with the EPO receptor have been identified and described. Specially, a group of peptides containing the major peptide fragment have been identified, which can bind to the EPO receptor and stimulate differentiation and proliferation of cells. However, the EC50 of the peptide that can stimulate differentiation and proliferation of cells is very low, ranging from 20 nM to 250 nM. Therefore, the clinical applications of these peptides are limited. The present invention provides EPO mimetic peptide derivatives, and their pharmaceutical salts, with biological activity and bioavailability, as well as methods for preparing the same.

SUMMARY

The present invention provides EPO mimetic peptide derivatives, and their pharmaceutical salts, with biological activity and bioavailability, as well as methods for preparing the same.

The invention also provides pharmaceutical compositions comprising the above-mentioned EPO mimetic peptide derivatives and their pharmaceutical salts, for treatment of disorders characterized by a low level of EPO or insufficient or defective red blood cell populations.

The invention discloses an EPO mimetic peptide derivative of general formula (I) and its pharmaceutical salts with in vivo biological activity, $$R^1—R^2—(CH_2)_{n1}—R^3—(CH_2)_{n2}—R^4—R^5 \quad (I)$$

wherein $R^1$, $R^5$ are selected from an EPO mimetic peptide monomer peptide and its analogues with in vivo biological activity; n1, n2 are integers independently selected from 0-10; $R^2$, $R^4$ are selected from —CO or —CH$_2$; $R^3$ is selected from O, S, CH$_2$, N(CH$_2$)n$_3$NHR$^6$, NCO(CH$_2$)n$_4$NHR$^6$, CHOCONH(CH$_2$)n$_5$NHR$^6$, CHSCON(CH$_2$)n$_5$NHR$^6$ and CHNHCON(CH$_2$)n$_5$NHR$^6$; wherein n3 is an integer selected from 1-10, n4 is an integer selected from 2-10, n5 is an integer selected from 2-10, $R^6$ is selected from H and methoxy polyethylene glycol derivatives.

In one aspect, $R^1$ and $R^5$ are independently selected from EPO mimetic peptides and their analogues having a general formula $Y^1X^1X^2X^3GX^4X^5TWX^6X^7Y^2Y^3$, which have in vivo biological activity. Each amino acid is designated by a standard single letter, the amino acid sequences of $R^1$, $R^5$ can be the same or different. In other embodiments, the amino acid sequences of $R^1$, $R^5$ are identical, and N-terminals of $R_1$, $R_5$ are acetylated; $X^2$, $X^3$, $X^4$, $X^5$, $X^6$, $Y^3$ are independently selected from any one of 20 genetically coding L-amino acids and non-natural amino acids. $Y^1$ and $Y^2$ are independently selected from any one of 20 naturally occurring genetically coded L-amino acids, non-natural amino acids, and peptides formed by these amino acids. $X^1$, $X^7$ are selected from amino acids C, K, D, E, Orn, and Hoc.

Further optimizing the above-mentioned preferred embodiment, $R^1$, $R^5$ are cyclic peptides cyclized by disulfide bonds or amide bonds. When $R^1$, $R^5$ are cyclic peptides cyclized by disulfide bonds, $X^1$, $X^7$ are independently selected from amino acids C and Hoc. When $R^1$, $R^5$ are cyclic peptides cyclized by amide bonds, $X^1$, $X^7$ are independently selected from amino acids K, D, E and Orn.

In the aspect encompassing the above-mentioned preferred embodiment, $Y^3$ is selected from the amino acids K, H or R, more preferably $Y^3$ is K.

In the aspect encompassing the above-mentioned embodiment, the amino acid sequence length of $R^1$ and $R^5$ is further optimized, namely, selected from 13-40 amino acids, optionally being 22 amino acids, optionally not limited to the following structure with a cyclic peptide, optionally NO:1-NO:8 cyclic peptides, namely:

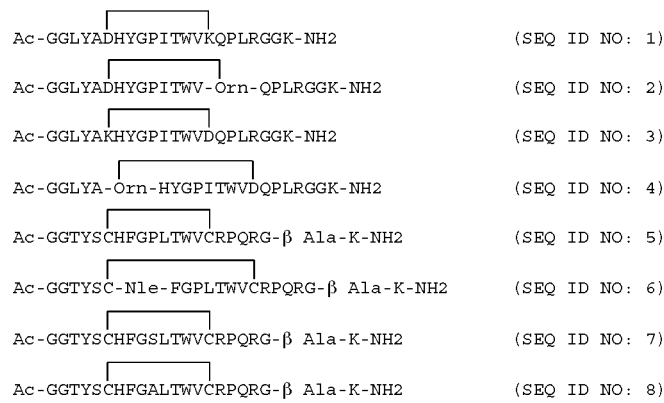

```
Ac-GGLYADHYGPITWVKQPLRGGK-NH2            (SEQ ID NO: 1)

Ac-GGLYADHYGPITWV-Orn-QPLRGGK-NH2       (SEQ ID NO: 2)

Ac-GGLYAKHYGPITWVDQPLRGGK-NH2            (SEQ ID NO: 3)

Ac-GGLYA-Orn-HYGPITWVDQPLRGGK-NH2       (SEQ ID NO: 4)

Ac-GGTYSCHFGPLTWVCRPQRG-β Ala-K-NH2      (SEQ ID NO: 5)

Ac-GGTYSC-Nle-FGPLTWVCRPQRG-β Ala-K-NH2  (SEQ ID NO: 6)

Ac-GGTYSCHFGSLTWVCRPQRG-β Ala-K-NH2      (SEQ ID NO: 7)

Ac-GGTYSCHFGALTWVCRPQRG-β Ala-K-NH2      (SEQ ID NO: 8)
```

-continued

```
Ac-GGLYADHYGPMTWVKQPLRGGK-NH2              (SEQ ID NO: 9)

Ac-GGLYADHYGPMTWV-Orn-QPLRGGK-NH2          (SEQ ID NO: 10)

Ac-GGLYA-Orn-HYGPMTWVDQPLRGGK-NH2          (SEQ ID NO: 11)

Ac-GGTYSKHFGPMTWVDRPQRG-β Ala-K-NH2        (SEQ ID NO: 12)

Ac-GGTYSCHFGPITWVCRPQRG-β Ala-K-NH2        (SEQ ID NO: 13)

Ac-GGTYSCHFGPMTWV-Hoc-RPQRG-β Ala-K-NH2    (SEQ ID NO: 14)

Ac-GGTYSCHFGPITWV-Hoc-RPQRG-β Ala-K-NH2    (SEQ ID NO: 15)

Ac-GGTYSC-Nle-FGPMTWV-Hoc-RPQRG-β Ala-K-NH2 (SEQ ID NO: 16)

Ac-GGTYSC-Nle-FGPITWVCRPQRG-β Ala-K-NH2    (SEQ ID NO: 17)

Ac-GGTYSCHFGPLTWVCRPQRG-β Ala-K-NH2        (SEQ ID NO: 18)

Ac-GGTYSCHFGSITWVCRPQRG-β Ala-K-NH2        (SEQ ID NO: 19)

Ac-GGTYSKHFGSMTWVERPQRG-β Ala-K-NH2        (SEQ ID NO: 20)

Ac-GGTYRCSMGPMTWVCLPMAGGK-NH2              (SEQ ID NO: 21)

Ac-GGTYRCSMGPLTWVCLPMAGGK-NH2              (SEQ ID NO: 22)

Ac-GGTYSCHFGAMTWVCRPQRG-β Ala-K-NH2        (SEQ ID NO: 23)

Ac-GGTYSCHFGAITWVCRPQRG-β Ala-K-NH2        (SEQ ID NO: 24)

Ac-GGTYSCHFGPITWVCRPQRG-β Ala-K-NH2        (SEQ ID NO: 25)

Ac-GGTYSCHFGPLTWVCRPQRG-β Ala-K-NH2        (SEQ ID NO: 26)

Ac-GGMYSCRMGPMTWVCGPSRGGK-NH2              (SEQ ID NO: 27)

Ac-GGMYSCRMGPLTWVCGPSRGGK-NH2              (SEQ ID NO: 28)

Ac-GGTYSCHFGPLTWV-Hoc-RPQRG-β Ala-K-NH2    (SEQ ID NO: 29)
and
Ac-GGTYS-Hoc-HFGPLTWVCRPQRG-β Ala-K-NH2    (SEQ ID NO: 30).
```

In this aspect, there are four optional embodiments:

[1] n1 and n2 are 2, $R^2$ and $R^4$ are —CO, $R^3$ is CHOCONH$(CH_2)_{n5}$NH $R^6$, n5 is 2, $R^6$ is H or methoxy polyethylene glycol derivatives;

[2] n1 and n2 are 1, $R^2$ and $R^4$ are —CO, $R^3$ is NCO$(CH_2)_{n4}$NH $R^6$, n4 is 2, $R^6$ is H or methoxy polyethylene glycol derivatives;

[3] n1 and n2 are 2, $R^2$ and $R^4$ are —CH$_2$, $R^3$ is CHOCONH$(CH_2)_{n5}$NH $R^6$, n5 is 2, $R^6$ is H or methoxy polyethylene glycol derivatives; and

[4] n1 and n2 are 1, $R^2$ and $R^4$ are —CH$_2$, $R^3$ is NCO$(CH_2)_{n4}$NH $R^6$, n4 is 2, $R^6$ is H or methoxy polyethylene glycol derivatives.

The above-mentioned four embodiments are in parallel, not being including or progressive relationship.

The above-mentioned four embodiments can be further optimized. $R^6$ may be selected from methoxy polyethylene glycol derivatives, optionally $R^6$ is methoxy polyethylene glycol derivatives. The molecular weight of methoxy polyethylene glycol derivatives is from about 5,000 to 100,000 Daltons. The structure of methoxy polyethylene glycol derivatives is selected from the branched or linear type.

In this aspect, through further comprehensive optimization, the following four embodiments are available:

[1] n1 and n2 are 2, $R^1$ and $R^5$ are selected from SEQ ID NO:1-SEQ ID NO: 8, $R^2$ and $R^4$ are selected from —CO, —CH$_2$, $R^3$ is CHOCONH$(CH_2)$n$_5$NHR$^6$, wherein n5 is selected from 2-10, optionally 2; $R^6$ is a methoxy polyethylene glycol derivative with linear structure and molecular weight of about 20,000 daltons;

[2] n1 and n2 are 1, $R^1$ and $R^5$ are selected from SEQ ID NO: 1-SEQ ID NO: 8, $R^2$ and $R^4$ are selected from —CO, —CH$_2$, $R^3$ is NCO$(CH_2)_{n4}$NH $R^6$, wherein n$_4$ is selected from 2-10 and optionally 2; R$_6$ is a methoxy polyethylene glycol derivative with linear structure and molecular weight of about 20,000 daltons;

[3] n1 and n2 are 2, $R^1$ and $R^5$ are selected from SEQ ID NO: 1-SEQ ID NO: 8, $R^2$ and $R^4$ are selected from —CO, —CH$_2$, $R^3$ is CHOCONH$(CH_2)_{n5}$NH $R^6$, wherein n5 is selected from 2-10 and optionally 2; $R^6$ is a methoxy polyethylene glycol derivative with branched structure and molecular weight of about 40,000 daltons; and

[4] n1 and n2 are 1, $R^1$ and $R^5$ are selected from SEQ ID NO: 1-SEQ ID NO: 8, $R^2$ and $R^4$ are selected from —CO, —CH$_2$, $R^3$ is NCO$(CH_2)_{n4}$NH $R^6$, wherein n$_4$ is selected from 2-10 and optionally 2; $R^6$ is a methoxy polyethylene glycol derivative with branched structure and molecular weight of about 40,000 daltons.

The structure of the most preferred EPO mimetic peptide derivatives and their pharmaceutical salts are selected from:
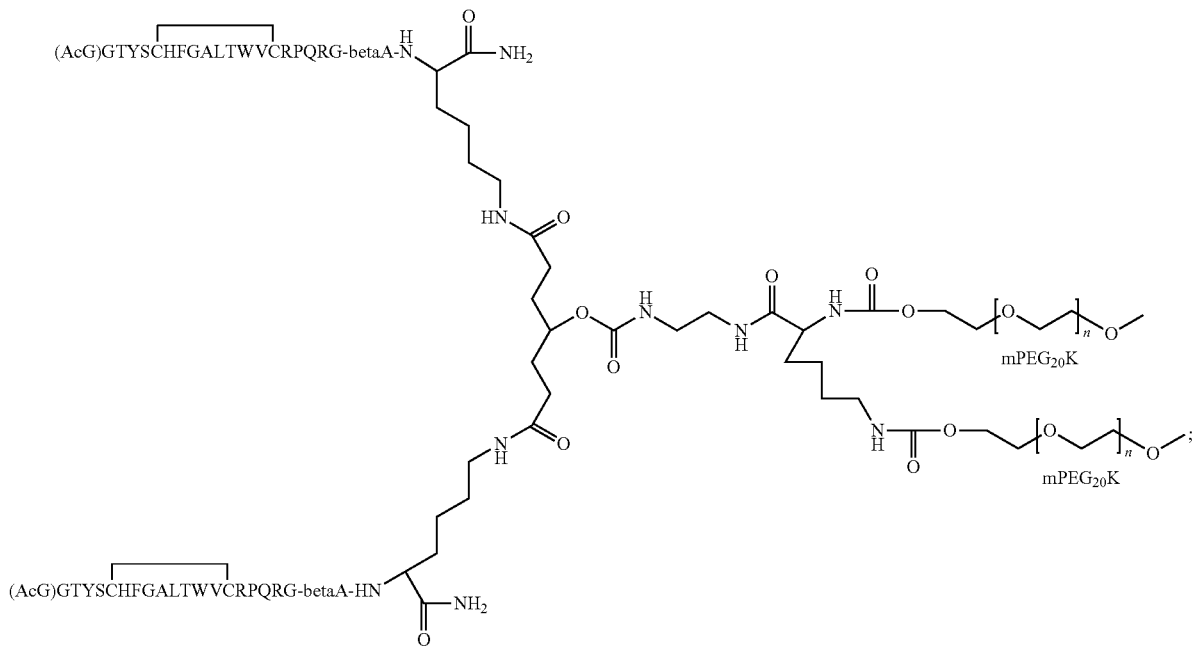
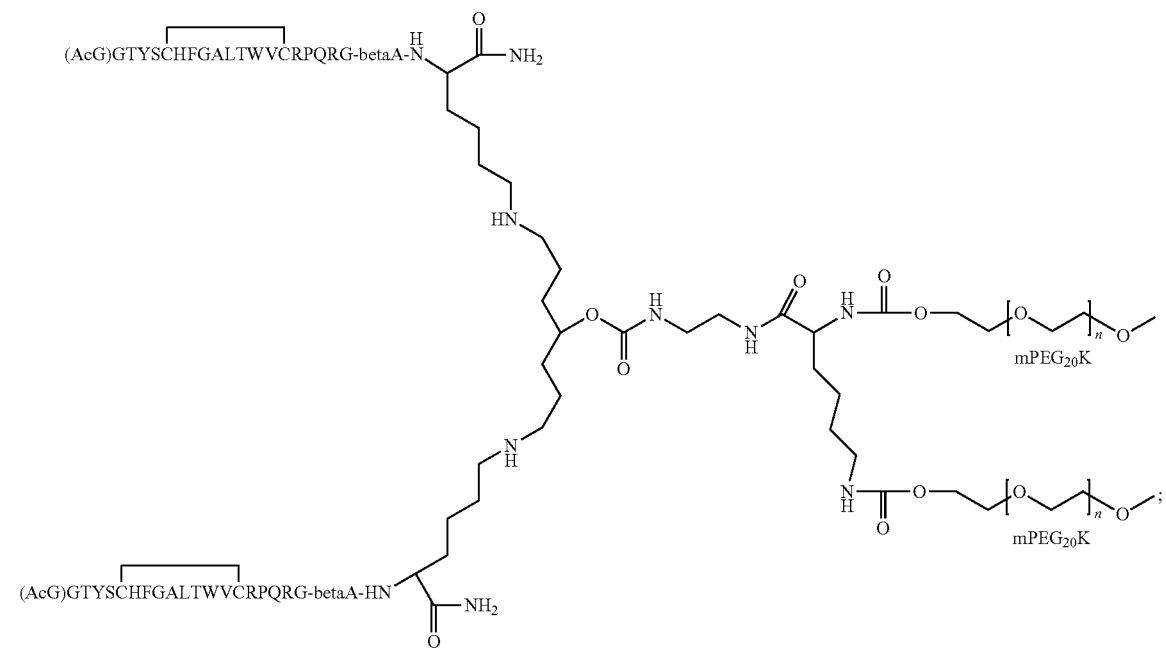

-continued

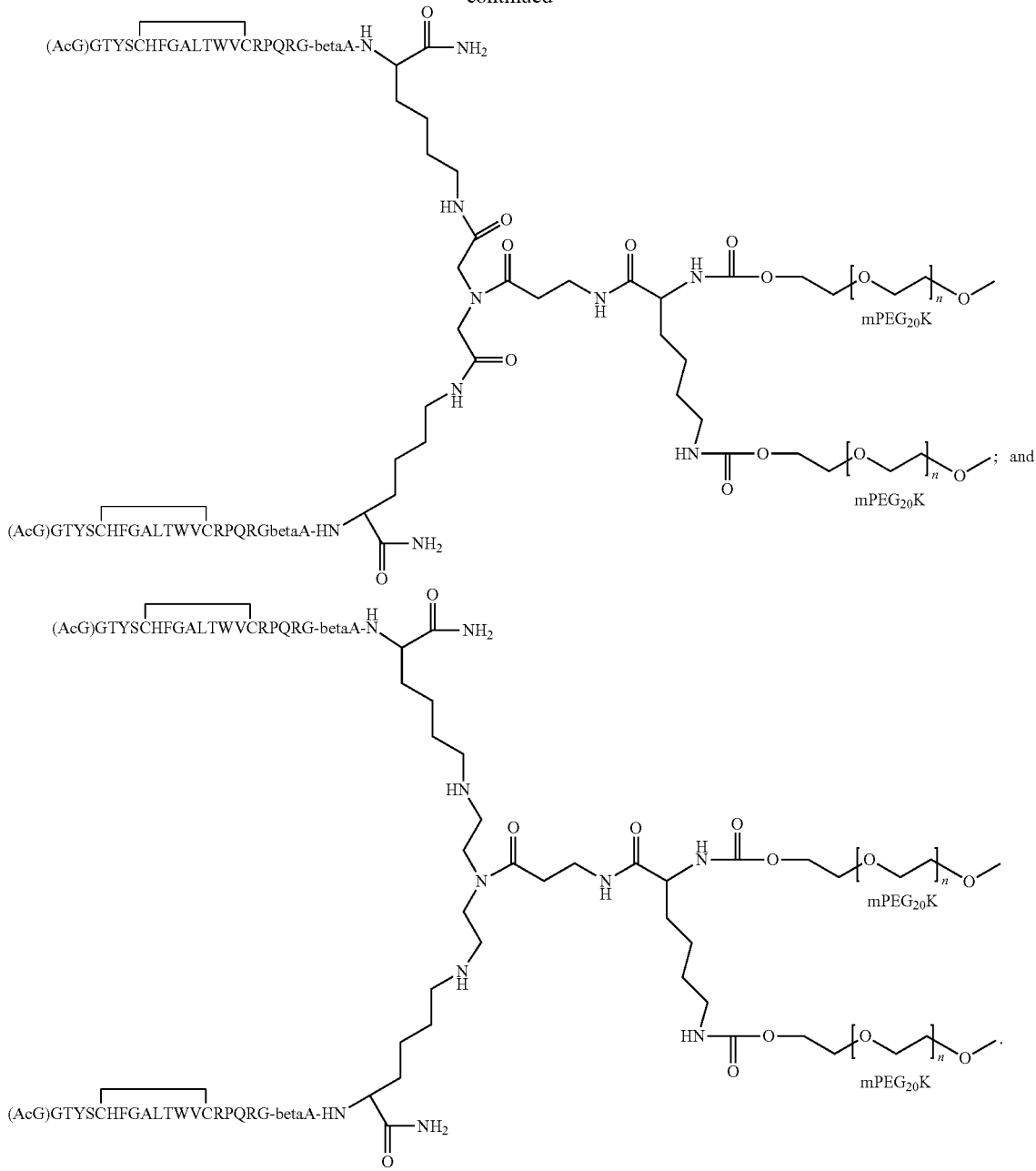

The EPO mimetic peptide derivatives provided herein are amphiphilic compounds, which can form salts by reacting with acidic or alkaline compounds through commonly known technology by one skilled in the art. Commonly used acids are selected from hydrochloric acid, hydrobromic acid, hydriodic acid, sulfuric acid, phosphoric acid, p-toluenesulfonic acid, methanesulfonic acid, oxalic acid, p-bromophenyl sulfonic acid, carbonic acid, succinic acid, citric acid, benzoic acid, acetic acid. The formed salts include sulfate, pyrophosphate, trifluoroacetate, sulfite, bisulfite, phosphate, biphosphate, dihydricphosphate, metaphosphate, pyrophosphate, chloride, bromide, iodide, acetate, propionate, caprylate, acrylate, formate, isobutyrate, caproate, enanthate, propiolate, oxalate, malonate, succinate, suberate, fumarate, maleate, butyne-1,4-dioate, hexyne-1,6-dioate, benzoate, chlorine benzoate, methyl benzoate, di nitrobenzoate, hydroxybenzoate, methoxybenzoate, phenylacetate, phenpropionate, phenylbutyrate, citrate, lactate, γ-hydroxybutyrate, glycolate, tartrate, methanesulfonate, propylsulfonate, naphtalin-1-sulfonate, naphtalin-2-sulfonate, mandelate and the like, preferably trifluoroacetate.

Alkaline substances can also react with EPO mimetic peptide derivatives to generate salts. These alkaline substances are selected from ammonium, hydroxides of alkali metal or alkaline earth metal, as well as carbonate, bicarbonate, typically selected from sodium hydroxide, potassium hydroxide, ammonium hydroxide, sodium carbonate, potassium carbonate and so on.

The invention also discloses the preparation process of the above-mentioned EPO mimetic peptide derivatives and their pharmaceutical salts, including the following steps:

(1) preparing $R^1$, $R^5$ through genetic engineering or chemical synthesis method. $R^1$, $R^5$ are mimetic peptides and their analogs with the biological function of EPO;
(2) preparing functional small molecule of general formula (II)

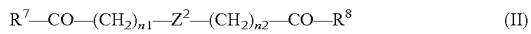
$$R^7\text{—CO—}(CH_2)_{n1}\text{—}Z^2\text{—}(CH_2)_{n2}\text{—CO—}R^8 \qquad (II)$$

wherein n1, n2 are integers independently selected from 0-10;
$R^7$, $R^8$ are selected from OH or H:
$Z^2$ is selected from O, S, $CH_2$, $N(CH_2)_{n6}NHR^9$, $NCO(CH_2)_{n7}NHR^9$, $CHOCONH(CH_2)_{n8}NHR^9$, $CHSCON(CH_2)_{n8}NHR^9$ or $CHNHCON(CH_2)_{n8}NHR^9$, wherein n6 is an integer selected from 1-10, n7 is an integer selected from 2-10, $n_8$ is an integer selected from 2-10, $R^9$ is selected from Boc and Cbz,
(3) connecting $R^1$, $R^5$ with the functional small molecule of formula (II), to prepare the compound of formula (III);

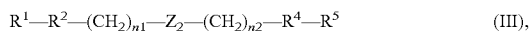
$$R^1\text{—}R^2\text{—}(CH_2)_{n1}\text{—}Z_2\text{—}(CH_2)_{n2}\text{—}R^4\text{—}R^5 \qquad (III),$$

wherein $R^2$, $R^4$ are independently selected from —CO or —$CH_2$,
(4) connecting formula (III) with active methoxy polyethylene glycol via covalent bonds after Boc or Cbz is removed.

The invention also relates to a pharmaceutical composition, comprising:
(1) therapeutic amounts of the above-mentioned EPO mimetic peptide derivatives and their pharmaceutical salts of the general formula (I); and
(2) a pharmaceutically acceptable drug carrier.

The invention also discloses use of the drugs, namely using any of said mimetic peptide derivatives and their pharmaceutical salts in a therapeutically effective amount to treat disorders characterized by low levels of EPO or insufficient or defective red blood cells, especially for treatment of the following diseases: advanced renal failure or dialysis; AIDS-related anemia, autoimmune diseases or malignant tumor; cystic fibrosis; early premature anemia; chronic inflammatory disease-related anemia; spinal cord injury; acute blood loss; aging and cancer with abnormal production of red blood cells.

EPO mimetic peptide derivatives and their pharmaceutical salts provided in the present invention are capable of promoting increase of the mouse peripheral blood reticulocyte counts, indicating that they stimulate erythropoiesis. At the same time, they are also capable of greatly extending the half-life of the conjugates in the body. EPO mimetic peptide derivatives and the EPO protein have no significant influence on mature red blood cells, blood cell hematocrit, hemoglobin content, and also have no significant influence on the peripheral white blood cell count.

Solid phase synthesis is used to synthesize EPO mimetic peptide monomers. The basic principle is to firstly connect the hydroxyl of the hydroxyl-terminal amino acid of the peptide chain to be synthesized with an insoluble polymer resin via covalent bond. Then amino acids attached to the solid phase carrier are used as the amino component to extend the polypeptide chain through removing the amino protection group and reacting with excessive active carboxyl component. The process is repeated (condensation→washing→deprotection→washing→the next round of condensation) to achieve the desired synthetic peptide chain. Finally the peptide chain is removed from the resin. After a purification treatment, the desired peptide is produced. The middle control of the reaction steps of condensation and deprotection employs a Ninhydrin detection method, namely when the resin peptide chain has free amino groups, a blue color will appear after staining by the ninhydrin reagent. When there is no free amino group, no color reaction will be developed (Ninhydrin reagent itself being yellow). Therefore, after carrying out the condensation reaction and detecting by ninhydrin, if yellow color is present (the color of ninhydrin reagent itself), it means that this coupling step is completed and deprotection operation before coupling of the next amino acid can be carried out. If a blue color is present, there is still some free amino on the peptide chain. It needs further repeated coupling or changing the current condensing agent until the resin-peptide presents a yellow color after detection by ninhydrin.

The method of cyclization of monomer peptide is well-known by one skilled in the art. Cyclization of disulfide bonds is mainly through oxidization of the sulfhydryl in the side chain of the amino acid of the monomer peptide into disulfide bonds by oxidant. Specifically, monomer peptides are placed in DMSO solution or 5% amine bicarbonate solution to be auto-oxidized, or added to acetic acid solution containing $I_2$ to be oxidized. Preferably peptides are added to an acetic acid solution containing $I_2$ to be oxidized. Cyclization of the amide bond is mainly through the formation of the amide bond between the carboxyl group and amino group of the amino side chain of the peptide in the presence of a condensing agent. The condensing agent added is well-known by one skilled in the art, usually including DIC, EDC, HATU, PyBOP etc.

Synthesis of a dimeric peptide is mainly through formation of a —NH—CH2-bond or —NH—CO—-bond between the amino side-chain of amino acid residue of EPO mimetic peptide monomer and functional small molecule. One skilled in the art can easily synthesize functional small molecule and connect it with monomer peptide cyclic peptide through known technology.

Dimeric peptide is reacted with active methoxy polyethylene glycol derivatives. The reaction system can be selected from organic solvents or buffer systems. When PEGylation reaction of the dimeric peptide is carried out in organic solvents, the following alkalis can be added in appropriate amount, including, but not limited to, such as triethylamine, diisopropyl ethylamine, pyridine, and 2,4,6-trimethyl pyridine. When the polyethylene glycol derivatization reaction is carried out in the buffer system, the buffer system can be selected from a variety of known available buffers, preferably a pH 7.7 phosphate buffer.

The biological activity of EPO, or EPO mimetic peptide derivatives and their pharmaceutical salts provided by this invention can be determined by various assays known in this field. Testing of in vivo activity is performed as follows: mice are subcutaneously injected with EPO and EPO mimetic peptide derivatives and their pharmaceutical salts provided by this invention on three consecutive days. The mice are then sacrificed. The whole blood is taken to carry out peripheral blood cells and reticulocyte count. The blood cell count is performed by automatic blood cell counter. Pharmacodynamic studies are carried out by intravenous administration to macaques with a dose of 1.35 mg/kg. The dose of EPO protein as a control drug is 240 μ/kg. The drugs are administered three times per week and the administration continues for six weeks. The blood samples are collected to carry out related hematological index analysis.

SUMMARY OF ABBREVIATIONS USED IN THE INVENTION

| Abbreviations | English name | Structure |
|---|---|---|
| Orn | L-Ornithine | 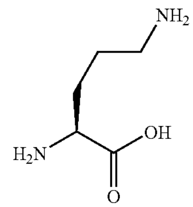 |
| Hoc | L-Homocysteine | 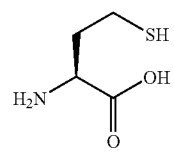 |
| DIC | N,N'-Diisopropylcarbodiimide | 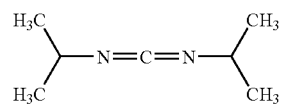 |
| EDC | 1-Ethyl-3-(3-dimethylaminopropyl) carbodiimide hydrochloride | 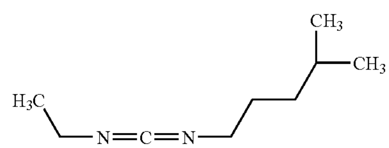 |
| PyBOP | Benzotriazol-1-yl-oxytripyrrolidinophosphonium hexafluorophosphate | 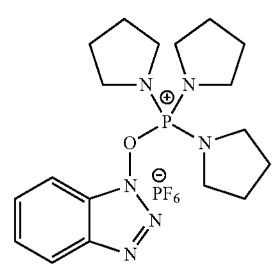 |
| HATU | 2-(1H-7-Azabenzotriazol-1-yl)-1,1,3,3-tetramethyl uronium hexafluorophosphate Methanaminium | 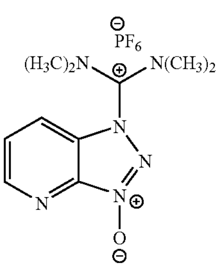 |
| DMAP | 4-Dimethylaminopyridine | 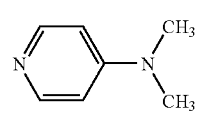 |
| Nle | Norleucine | 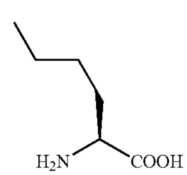 |

| Abbreviations | English name | Structure |
|---|---|---|
| mPEG₂-OSU(40k) | Branched Methoxy polyethylene glycol N-Hydroxysuccinimide(40k) | (mPEG₂₀K branched structure) |

DETAILED DESCRIPTION OF THE PREFERRED EMBODIMENTS

Figure 1:
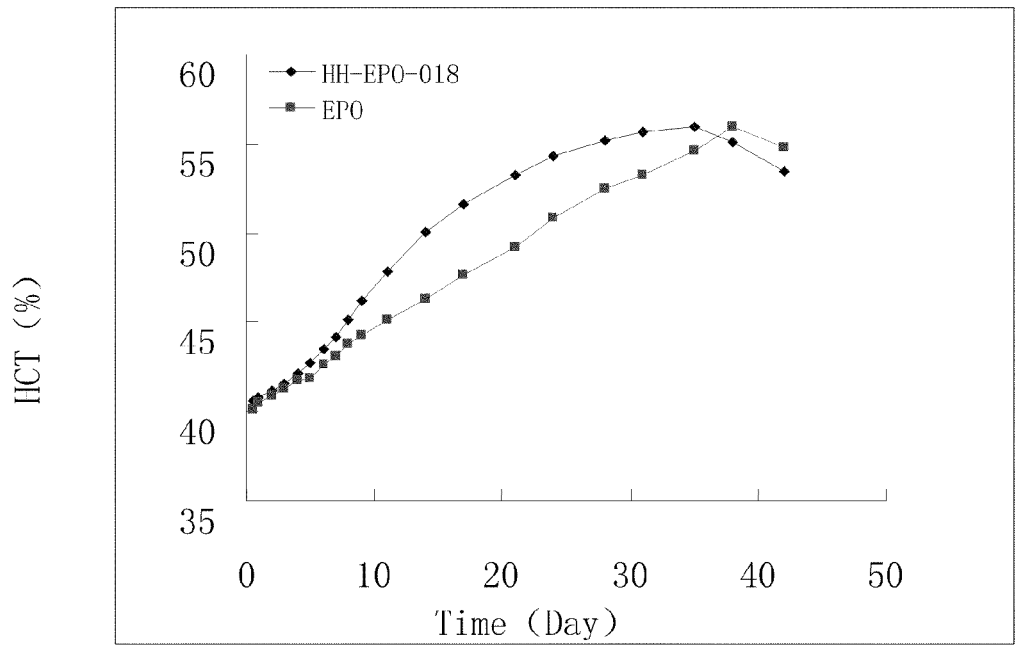
FIG. 1 shows the influence of EPO mimetic peptide derivatives (HH-EPO-018) on hematocrit of macaques.

For a more detailed description of the present invention, the following examples are proved. However, the scope of the present invention is not limited to this.

EXAMPLE 1

Synthesis of EPO Mimetic Peptide Monomers

Synthesis of EPO mimetic peptide monomers is performed by a solid-phase peptide synthesis method. This peptide synthesis method has been reported in many literatures, see Stewart, J. M., and Young, J. D., solid phase peptide synthesis 2d edition, novabiochem peptide synthesis notes. The EPO mimetic peptide derivatives provided by this invention may be performed by manual synthesis methods. The resin is rink amind resin. The α-amino of the amino acid derivatives are protected by Fmoc (fluorene-formyl carbonyl). The thiol group of cysteine side chain, the amino group of glutamine side chain, and the imidazole group of histidine side chain are protected by Trt (trityl). The guanidine group of the arginine side-chain is protected by Pbf (2,2,4,6,7-Pentamethyldihydrobenzofuran-5-sulfonyl). The indole group of tryptophan side chain, and the amino group of the lysine side chain, are protected by Boc (tert-Butoxycarbonyl). The hydroxyl group of the threonine side chain, the phenol group of the tyrosine side chain, and the hydroxyl group of the serine side chain are protected by tBu (tert-butyl). The carboxyl of the C-terminal of the peptide chain of the EPO mimetic peptide derivative to be synthesized is attached to insoluble resin (rink amind resin) by covalent bonds. Then amino acids attached to the solid phase carrier is used as the amino component to extend the polypeptide chain after removing amino protection groups by a 20% piperidine DMF solution and reacting with excessive amino acid derivative. The operation is then repeated (condensation→washing→deprotection→washing→the next round of condensation) to achieve the desired synthetic peptide chain length. Finally, the peptide chain is removed from the resin using a mixed solution of trifluoroacetic acid, water, ethylene mercaptan, 3-isopropyl silane (92.5:2.5:2.5:2.5). After ether sedimentation, the crude EPO mimetic monomers are obtained. The crude peptide monomer is separated and purified by a C18 reverse-phase preparative column. Then an EPO mimetic peptide derivative monomer peptide is obtained. The control of the reaction steps of condensation and deprotection employs a Ninhydrin detection method, namely when the resin peptide chain has free amino groups, a blue color will appear after staining by the ninhydrin reagent. When there is no free amino group, no color reaction will be developed (Ninhydrin reagent itself being yellow). Therefore, after carrying out the condensation reaction and detecting by ninhydrin, if yellow color is present (the color of ninhydrin reagent itself), it means that this coupling step is completed and the deprotection operation can be carried out before coupling of the next amino acid. If a blue color is present, it means that there are still some free amino on the peptide chain. It needs further repeated coupling or changing the current condensing agent until the resin-peptide presents a yellow color after detection by ninhydrin.

EXAMPLE 2

Preparation of Functional Small Molecules (LG-1)

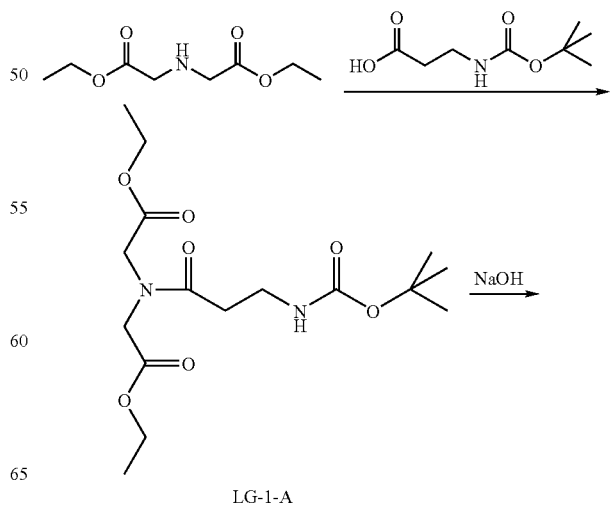

LG-1-A

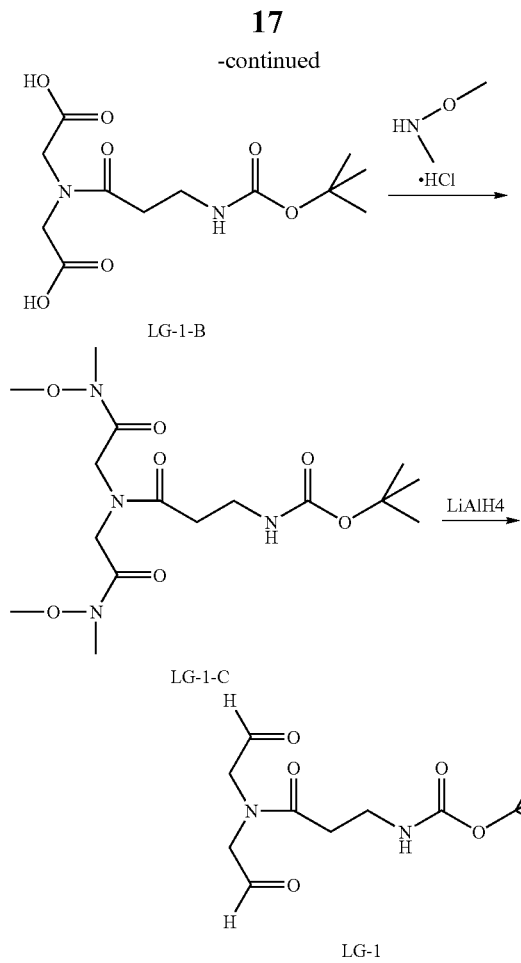

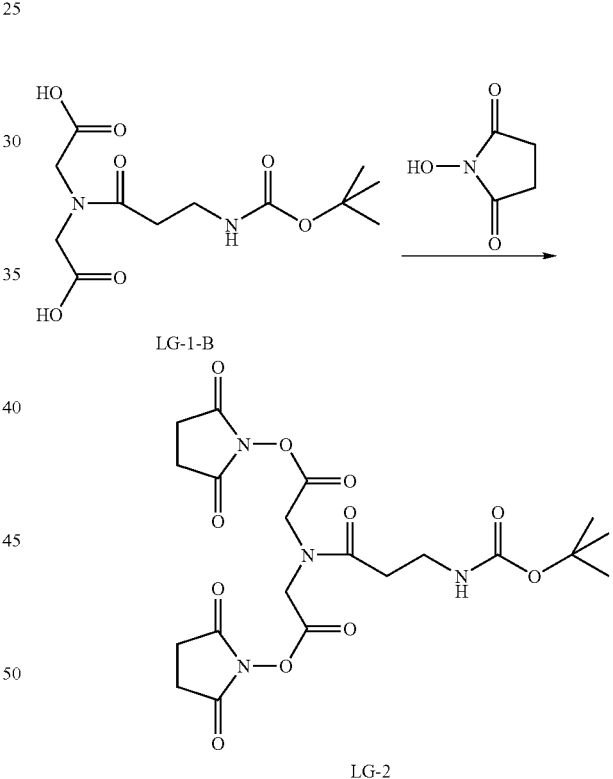

DIC (4.4 g, 32 mmol), and HOBT (4.7 g, 32 mmol) are added into the solution successively. The reaction mixture is stirred overnight at room temperature. Then the reaction mixture is added into water and extracted by 350 mL of ethyl acetate. The organic phase is washed with 200 mL of 2 N HCl aqueous solution, 200 mL of saturated sodium bicarbonate solution, 100 mL of saturated saline successively. The organic phase is separated, dried with anhydrous magnesium sulfate for 2 hours, and then filtrated. The filtrate becomes oily after concentration at reduced pressure. After column chromatography, the target product LG-1-C (4.2 g, yield: 70%) is collected.

Step 4: Preparation of LG-1

LG-1-C (4.0 g, 10.2 mmol) is dissolved in 60 mL of tetrahydrofuran. The solution is cooled down to 0° C. by an ice-salt bath. LiAlH$_4$ (340 mg, 8.9 mmol) is added into the solution. After reacting at 0° C. for 30 minutes, 4 mL of water and 4 mL of 15% NaOH solution are added successively. The reaction solution is filtered. The filtrate is washed with tetrahydrofuran, concentrated, and purified by silica gel column chromatography to provide LG-1 (1.63 g, 6 mmol, Yield: 58.8%).

EXAMPLE 3

Preparation of Functional Small Molecule LG-2

LG-1-B (4 g, 13 mmol) is dissolved in 100 mL of N,N-dimethylformamide. Hydroxysuccinimide (3.1 g, 21 mmol), DIC (4 mL, 26 mmol), and DMAP (4-dimethylamino pyridine) (12 mg, 0.08 mmol) are added into the solution. After stirring overnight, the reaction solution is concentrated at reduced pressure. The residue is dissolved in 80 mL of ethyl acetate. The insoluble substances are filtered off. The organic phase is washed with 40 mL of saturated sodium bicarbonate solution, 40 mL of saturated saline, 40 mL of 0.5 N HCl solution, and 40 mL of saturated saline successively. The organic phase is separated and dried with anhydrous magnesium sulfate. The organic phase is filtered. The filtrate is concentrated at reduced pressure. A white solid LG-2 (4.4 g) is obtained. Yield is about 68%.

Step 1: Preparation of LG-1-A

Iminodiacetic acid diethyl ester (10.0 g, 52.8 mmol) and Boc-β-alanine (10.0 g, 52.8 mmol) are dissolved in 100 mL of dichloromethane. DIC (8.0 mL, 52.8 mmol) is added into the solution. The reaction solution is stirred at room temperature overnight. The reaction solution is filtered. The filtrate is washed with 100 mL of saturated NaHCO$_3$, 50 mL of a 0.5 N HCl solution, and 100 mL of saturated saline successively. The organic phase is isolated from the aqueous phase and dried with anhydrous MgSO$_4$. The organic phase is filtered and concentrated to provide a colorless oily substance LG-1-A (17 g).

Step 2: Preparation of LG-1-B

LG-1-A (17 g) is dissolved in 100 mL of a mixture of MeOH and THF (1:1). Then 25 mL of water, and 5 g of NaOH (125 mmol) are added into the solution. The solution is stirred at room temperature for 2 hours. Then the pH value of the solution is adjusted to 1 with a 6 N HCl solution. The reaction solution is extracted with ethyl acetate four times. The organic phase is washed with saline, dried by anhydrous magnesium sulfate, and concentrated at a reduced pressure to produce a white semi-solid. The product is dissolved in 50 mL of dichloromethane. Then 300 mL of n-hexane is added to the solution to produce a white paste. After concentrated at a reduced pressure, a white solid LG-1-B (14 g) is obtained. The yield is about 90%.

Step 3: Preparation of LG-1-C

LG-1-B (7 g, 23 mmol) is dissolve in 80 mL of tetrahydrofuran. Under stirring, N,N-methoxy-methyl-amine hydrochloride (4.6 g, 46 mmol) and triethylamine (5.1 g, 51 mmol),

EXAMPLE 4
Preparation of Functional Small Molecules (LG-3)
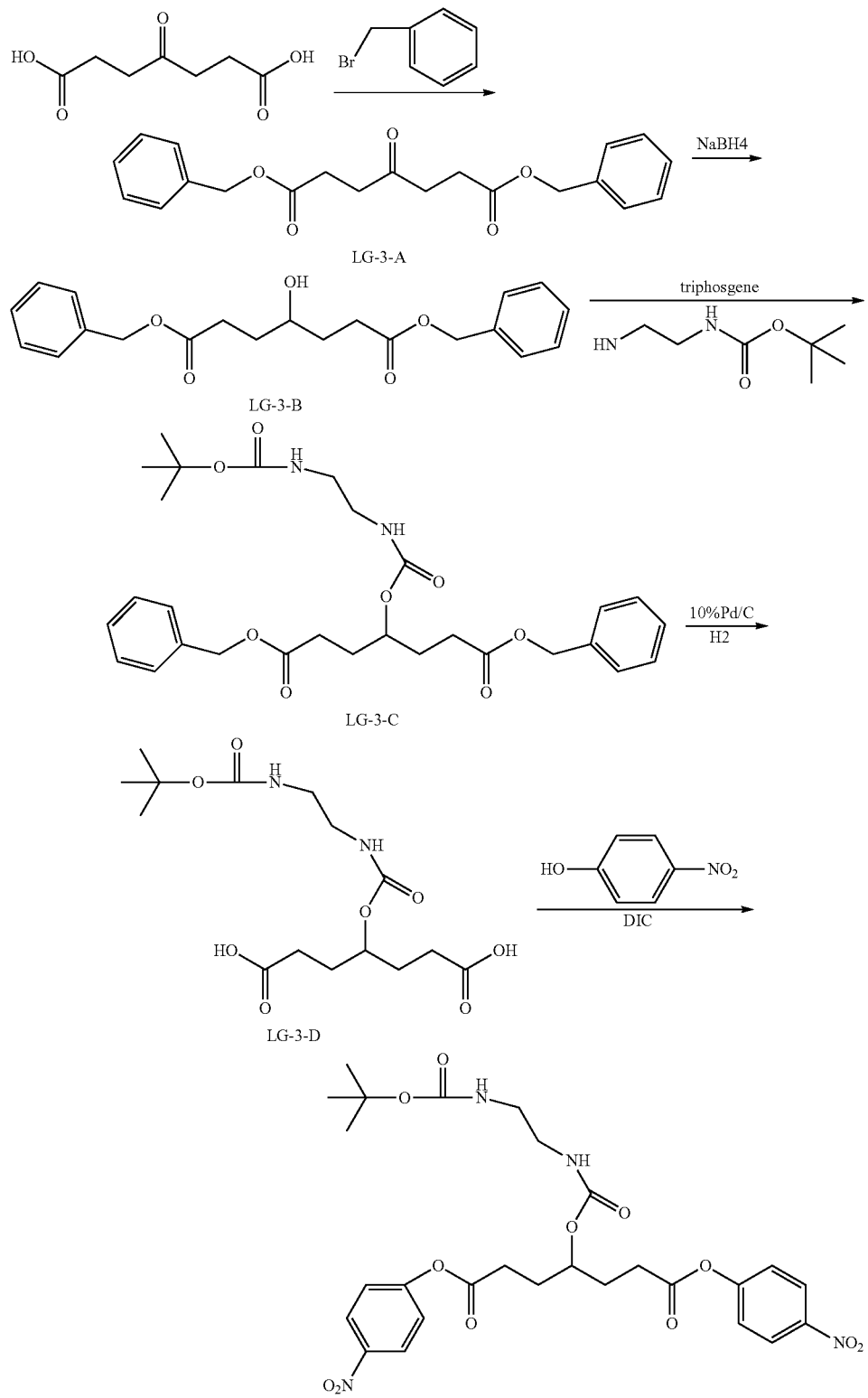

Step 1: Preparation of LG-3-A

Pentanone pimelic acid (7.0 g, 0.04 mol) is dissolved in 100 mL of methanol. 5% CsCO₃ in methanol is added into the solution under stirring. The pH of the reaction mixture is controlled at about 8.5 by the amount of CsCO₃ (determined by high resolution pH test paper). The mixture is stirred for 30 minutes after the addition is completed. Then the reaction mixture is filtered. The filtrate becomes oily after vacuum concentration. The oily filtrate is dissolved in about 100 mL of DMSO and the solution is warmed up to 60° C. Benzyl bromide (14 g, 0.08 mol) is added into the solution. After reacting for 8 hours, the reaction mixture is filtered. The solid is washed with a small amount of ether. 400 mL of ether is added into the mother liquor. Then the mother liquor is washed with 200 mL of saturated saline. The organic phase is separated and dried with anhydrous magnesium sulfate for 2 hours. Then the organic phase is filtered. When the filtrate is concentrated at reduced pressure to ⅕ of its original volume, it is placed in −20° C. freezer overnight to crystallize. The solid is filtered out and dried to provide a white solid LG-3-A (10.5 g, Yield 74%).

Step 2: Preparation of LG-3-B

LG-3-A (2 g, 0.0056 mol) is dissolved in 20 mL of tetrahydrofuran. The internal temperature of the solution is maintained below −10° C. NaBH₄ (626 mg, 0.0168 mol) is added into the solution under stirring. After 1 hour of reaction, 200 mL of chilled ether is added, followed by addition of 150 mL of saturated sodium bicarbonate solution to terminate the reaction. The solution is kept still to allow the organic phase separate from the aqueous phase. The organic phase is washed for one time with saturated saline, then dried with anhydrous Na₂SO₄ for 2 hours, and filtered. The filtrate is concentrated at reduced pressure to produce LG-3-B (1.9 g, Yield: 94.6%).

Step 3: Preparation of LG-3-C

LG-3-B (3.2 g, 0.009 mol) is dissolved in 50 mL of dichloromethane. Triethylamine (4.34 g, 0.043 mol) is added into the solution below 0° C. under stirring. Triphosgene (1.33 g, 0.0045 mol) is dissolved in 25 mL of dichloromethane. Then the triphosgene solution is added into the LG-3-B solution dropwise. tert-Butoxycarbonyl-ethylenediamine (2.8 g) is added into the reaction mixture after 1 hour. After 3 hours of reaction, the reaction mixture is adjusted to neutral with glacial acetic acid. A precipitate is generated. The precipitate is filtered off. The filtrate is concentrated at reduced pressure and then dissolved in ether. Then the solution is washed with water for three times and with saturated saline for one time. The organic phase is separated out, dried with anhydrous magnesium sulfate for 2 hours and then filtrated. The filtrate is concentrated at reduced pressure to provide an oily substance. The oily substance is purified by silica gel column chromatography (mobile phase: petroleum ether:ethyl acetate=10:1). The target fragments are collected and combined. The combined fragments are concentrated to produce LG-3-C (1.5 g, Yield 38.8%) as a white solid.

Step 4: Preparation of LG-3-D

LG-3-C (13 g, 0.031 mol) is dissolved in 8 mL of methanol. 200 mg 10% Pd—C is added under stirring. After 4 hours of reaction under H₂ at an atmospheric pressure, the activated carbon is filtered off The filtrate is concentrated to produce an oily substance LG-3-D (8.28 g, Yield: 96.7%).

Step 5: Preparation of LG-3

LG-3-D (5 g, 0.018 mol) is dissolved in 10 mL of tetrahydrofuran. p-Nitrophenol (4.7 g, 0.043 mol) is added. Then DIC (4.2 g, 0.043) is added into the solution under stirring. The reaction is stirred overnight. The resulting precipitate is filtered out. The filter cake is washed with a small amount of ethyl acetate and dried under reduced pressure. The residue is dissolved in 100 mL of ethyl acetate. The resulting solution is washed with 50 mL saturated saline once. The organic phase is separated and dried over anhydrous magnesium sulfate for 2 hours. Then the solution is filtered. The filtrate is concentrated at reduced pressure to produce an oily substance. The oily substance is purified by silica gel column chromatography (eluant: hexane and ethyl acetate, ration from 20:1 to 10:1). The target fragments are combined and collected, and concentrated at reduced pressure to produce LG-3 (3.5 g, Yield: 32%) as a white solid.

EXAMPLE 5

Preparation of Functional Small Molecule (LG-4)

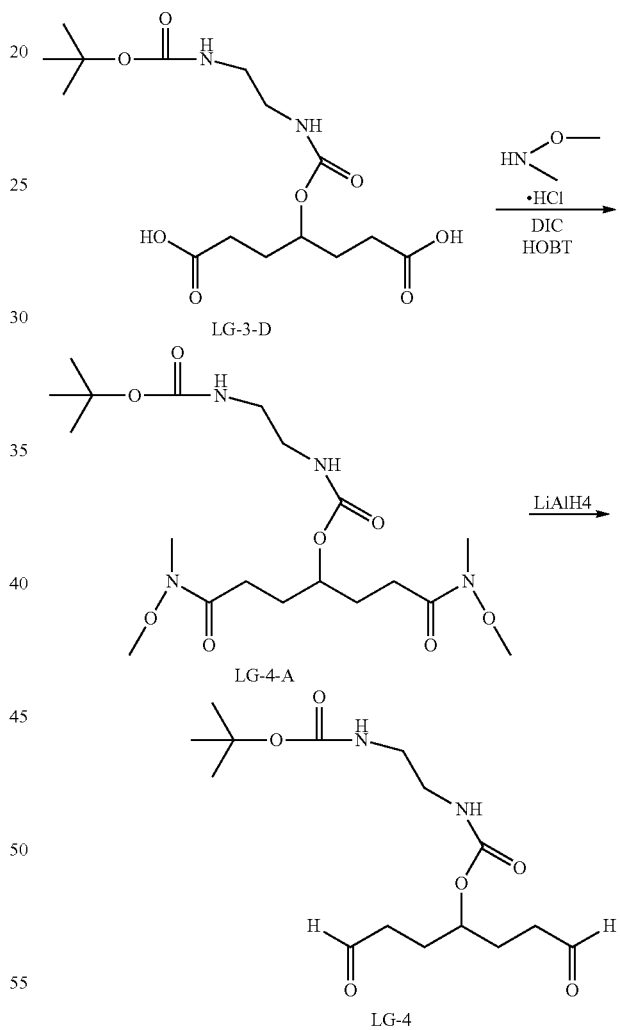

Step 1: Preparation of LG-4-A

LG-3-D (5 g, 0.018 mol) is dissolved in 60 mL of tetrahydrofuran. N,N-Methoxy-methyl-amine hydrochloride (3.51 g, 0.036 mol) and triethylamine (4.0 g, 0.04 mol) are added into the solution under stirring. Then DIC (3.4 g, 0.027 mol) and HOBT (3.65 g, 0.027 mol) are added into the reaction mixture. The reaction mixture is stirred overnight at room temperature, added into 200 mL of water, and extracted with 200 mL of ethyl acetate twice. The combined organic phase is washed with 50 mL of 2 N HCl solution, 100 mL of saturated NaHCO₃ solution, and 100 mL of saturated saline successively. The combined organic phase is dried over anhydrous magnesium sulfate for 2 hours, and filtered. The filtrate is concentrated at reduced pressure to produce an oily substance. The oily substance is purified by column chromatography (eluant: hexane:ethyl acetate at 10:1). The target components are combined to produce a white solid LG-4-A (6.24 g, Yield: 80%).

Step 2: Preparation of LG-4

LG-4-A (4.0 g, 9 mmol) is dissolved in 50 mL of tetrahydrofura. LiAlH₄ (300 mg, 7.9 mmol) is added into the solution in an ice-salt bath at a temperature of below zero. The temperature of the reaction mixture is maintained at 0° C. for 30 minutes. Then 0.3 mL of water, 0.9 mL of 15% NaOH solution, and 0.3 mL of water are added into the reaction mixture successively. A precipitate is generated. The precipitate is filtered out. The filter cake is washed with tetrahydrofuran once. The filtrate is combined and concentrated at reduced pressure. The residue is purified by column chromatography to produce LG-4 (1.65 g, Yield: 55.5%).

EXAMPLE 6

Preparation of HH-EPO-005

Shield™ RP18, 3.5 μm, 4.6*100 mm). The column temperature is 60° C. and the detection wavelength is 214 nm. Water (containing 0.05% trifluoroacetic acid) and acetonitrile (containing 0.05% trifluoroacetic acid) in different proportions are used as mobile phases. The target fractions are collected and combined. After most of the acetonitrile is distilled off under reduced pressure and the resulting residue is freeze-dried, 3.0 g of SEQ ID NO: 5 cyclic peptide is obtained (Yield: 15.6%).

Step 2: Preparation of HH-EPO-005

The cyclic peptide of SEQ ID NO: 5 (3.0 g, 1.22 mmol) is dissolved in 150 mL of N,N-dimethyl formamide. Triethylamine (147 mg, 1.46 mmol) and the functional small molecule (LG-3) (368 mg, 0.61 mmol) are added into the solution. After the reaction is stirred at room temperature for 6 hours, part of the N,N-dimethylformamide is removed. 200 mL of ether is added into the residue. The mixture is placed in a refrigerator for 2 hours and centrifuged. A white solid is obtained and dried under vacuum. Then the white solid is dissolved in 50 mL of 20% trifluoroacetic acid in dichloromethane solution. After the solution is stirred at room temperature for 30 minutes, part of the solvent is removed under reduced pressure. 200 mL of ether is added into the residue. The mixture is placed in the refrigerator for 2 hours and then centrifuged. A white solid is obtained and dried by vacuum. The white solid is subjected to a preparative purification by

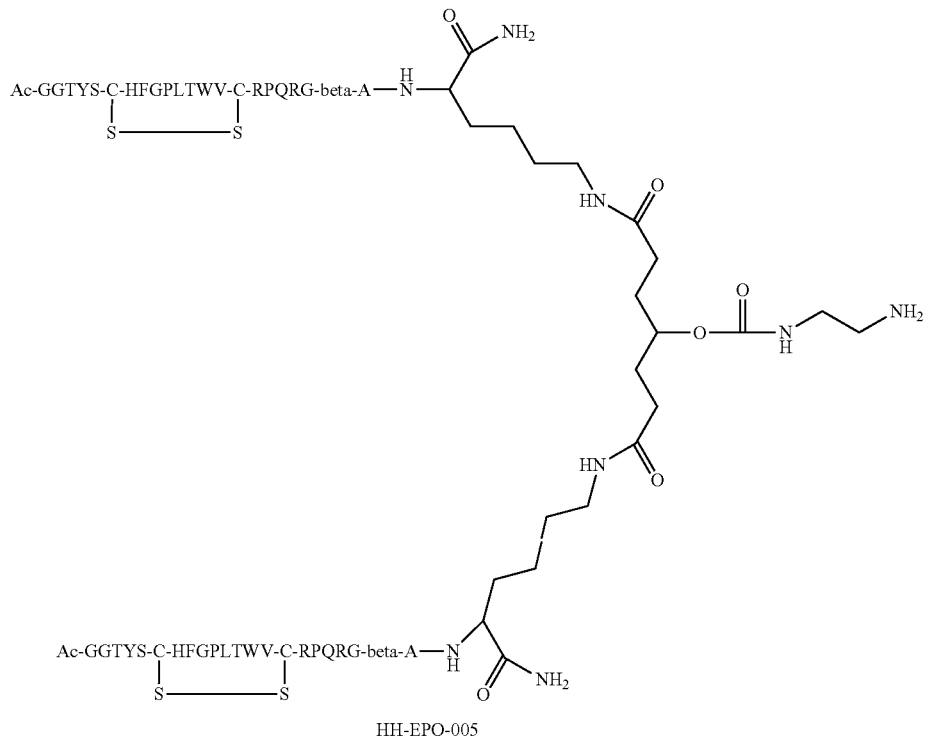

HH-EPO-005

Step 1: Preparation of SEQ ID NO: 5 Cyclic Peptide

The peptide monomer of SEQ ID NO: 5 (9 g, synthesized in accordance with the method given in the Examples) is dissolved in 3000 mL of 20% glacial acetic acid. Then a 5% iodine-methanol solution is added into the solution dropwise and slowly until the yellow color does not disappear. The reaction solution is directly subjected to a preparative purification by reversed-phase chromatography using octadecylsilane bonded silica gel as column filler (Waters Symmetryreversed-phase chromatography, using octadecylsilane bonded silica gel as column filler (Waters SymmetryShield™ RP18, 3.5 μm, 4.6*100 mm). The column temperature is 60° C. and the detection wavelength is 214 nm. Water (containing 0.05% trifluoroacetic acid) and acetonitrile (containing 0.05% trifluoroacetic acid) in different proportions are used as mobile phases. The target fractions are collected and combined. After most of the acetonitrile is distilled off under reduced pressure and the resulting residue is freeze-dried, 1.0 g of HH-EPO-005 is obtained (Yield is about 33%).

EXAMPLE 7

Preparation of HH-EPO-006

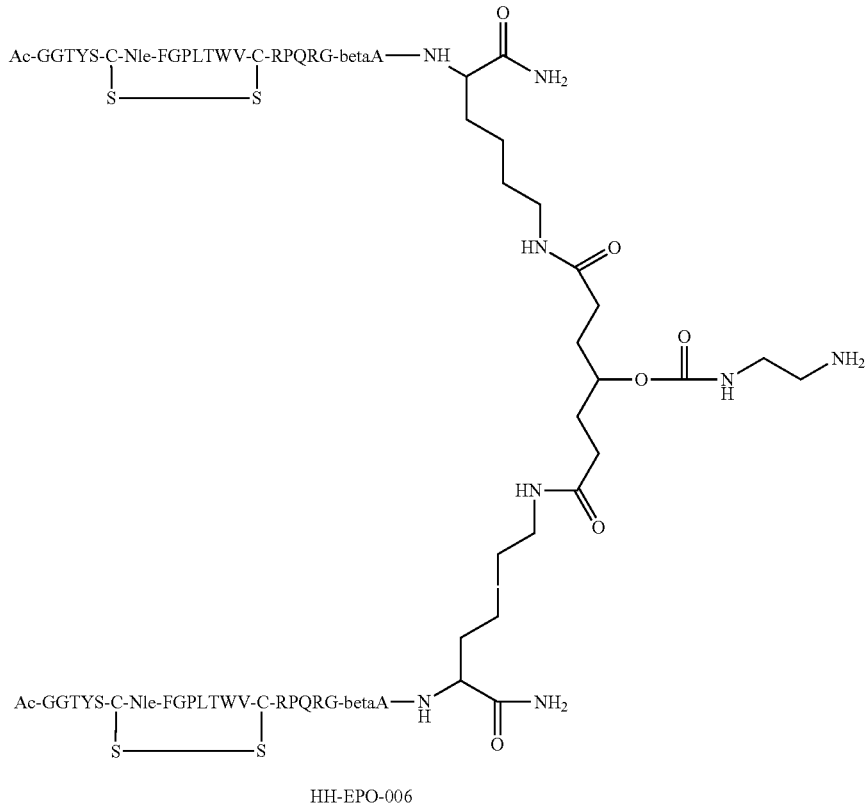

HH-EPO-006

Step 1: Preparation of SEQ ID NO: 6 Cyclic Peptide

The peptide monomer of SEQ ID NO: 6 (9 g, synthesized in accordance with the method given in the Examples) is added in 3000 mL of 20% glacial acetic acid. Then a 5% iodine-methanol solution is added dropwise slowly until the yellow color does not disappear. The reaction solution is directly subjected to a preparative purification by reversed-phase chromatography, using octadecylsilane bonded silica gel as column filler (Waters SymmetryShield™ RP18, 3.5 μm, 4.6*100 mm). The column temperature is 60° C. and the detection wavelength is 214 nm. Water (containing 0.05% trifluoroacetic acid) and acetonitrile (containing 0.05% trifluoroacetic acid) in different proportions are used as mobile phases. The target fractions are collected and combined. After most of the acetonitrile is distilled off under reduced pressure and the resulting residue is freeze-dried, 3.0 g of SEQ ID NO:6 cyclic peptide is obtained (Yield: 15.3%).

Step 2: Preparation of HH-EPO-006

The cyclic peptide of SEQ ID NO: 6 (3.0 g, 1.22 mmol) is dissolved in 150 mL of N,N-dimethyl formamide. Triethylamine (147 mg, 1.46 mmol) and the functional small molecule (LG-3) (368 mg, 0.61 mmol) are added into the solution. After the reaction is stirred at room temperature for 6 hours, part of the DMF is removed. 200 mL of ether is added into the residue. The mixture is placed in a refrigerator for 2 hours and then centrifuged. A white solid is obtained and dried under vacuum. Then the white solid is dissolved in 50 mL of 20% trifluoroacetic acid in dichloromethane solution. After the mixture is stirred at room temperature for 30 minutes, part of the solvent is removed under reduced pressure. 200 mL of ether is added into the residue. The mixture is placed in a refrigerator for 2 hours and then centrifuged. A white solid is obtained and dried under vacuum. The white solid is subjected to a preparative purification by reversed-phase chromatography, using octadecyl silane bonded silica gel as column filler (Waters SymmetryShield™ RP18, 3.5 μm, 4.6*100 mm). The column temperature is 60° C. and the detection wavelength is 214 nm. Water (containing 0.05% trifluoroacetic acid) and acetonitrile (containing 0.05% trifluoroacetic acid) in different proportions are used as mobile phases. The target fractions are collected and combined. Most of the acetonitrile is distilled off under reduced pressure. The residue is freeze-dried to provide 3.98 g of HH-EPO-006 at a yield of about 32.7%.

EXAMPLE 8

Preparation of HH-EPO-007

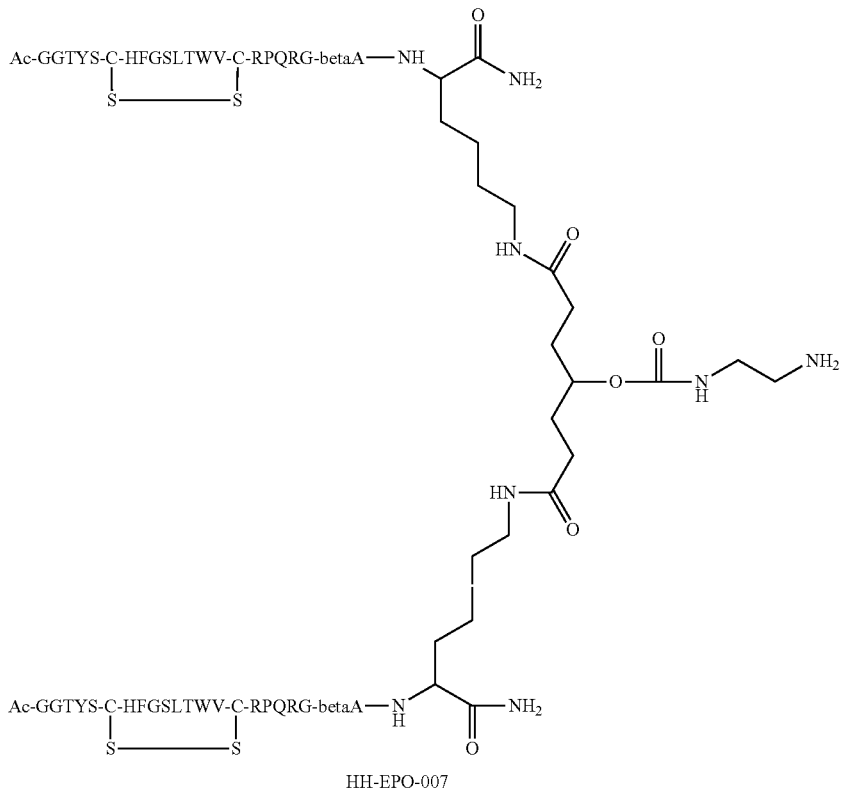

HH-EPO-007

Step 1: Preparation of SEQ ID NO: 7 Cyclic Peptide

The peptide monomer of SEQ ID NO: 7 (9 g, synthesized in accordance with the method given in the Examples) is dissolved in 3000 mL of 20% glacial acetic acid. Then a 5% iodine-methanol solution is added dropwise until the yellow color does not disappear. The reaction solution is directly subjected to a preparative purification by reversed-phase chromatography, using octadecylsilane bonded silica gel as column filler (Waters SymmetryShield™ RP18, 3.5 μm, 4.6*100 mm). The column temperature is 60° C. and the detection wavelength is 214 nm. Water (containing 0.05% trifluoroacetic acid) and acetonitrile (containing 0.05% trifluoroacetic acid) in different proportions are used as mobile phases. The target fractions are collected and combined. Most of the acetonitrile is distilled off under reduced pressure and the reside is freeze dried, 3.15 g of SEQ ID NO:7 cyclic peptide is obtained (Yield: 16.4%).

Step 2: Preparation of HH-EPO-007

The cyclic peptide of SEQ ID NO: 7 (3.0 g, 1.22 mmol) is dissolved in 150 mL of N,N-dimethyl formamide. Triethylamine (147 mg, 1.46 mmol) and the functional small molecule (LG-3) (368 mg, 0.61 mmol) are added into the solution. After the reaction is stirred at room temperature for 6 hours, part of the N,N-dimethylformamide is removed. 200 mL of ether is added into the residue. The mixture is placed in a refrigerator for 2 hours and then centrifuged. A white solid is obtained and dried under vacuum. Then this white solid is dissolved in 50 mL of 20% trifluoroacetic acid in dichloromethane solution. After the mixture is stirred at room temperature for 30 minutes, part of the solvent is removed under reduced pressure. 200 mL of ether is added into the residue. The mixture is placed in a refrigerator for 2 hours and then centrifuged. A white solid is obtained and dried under vacuum. The white solid is subjected to a preparative purification by reversed-phase chromatography, using octadecylsilane bonded silica gel as column filler (Waters SymmetryShield™ RP18, 3.5 μm, 4.6*100 mm). The column temperature is 60° C. and the detection wavelength is 214 nm. Water (containing 0.05% trifluoroacetic acid) and acetonitrile (containing 0.05% trifluoroacetic acid) in different proportions are used as mobile phases. The target fractions are collected and combined. After most of the acetonitrile is distilled off under reduced pressure and the residue is freeze-dried, 1.0 g of HH-EPO-007 is obtained (Yield is about 33%).

EXAMPLE 9

Preparation of HH-EPO-008

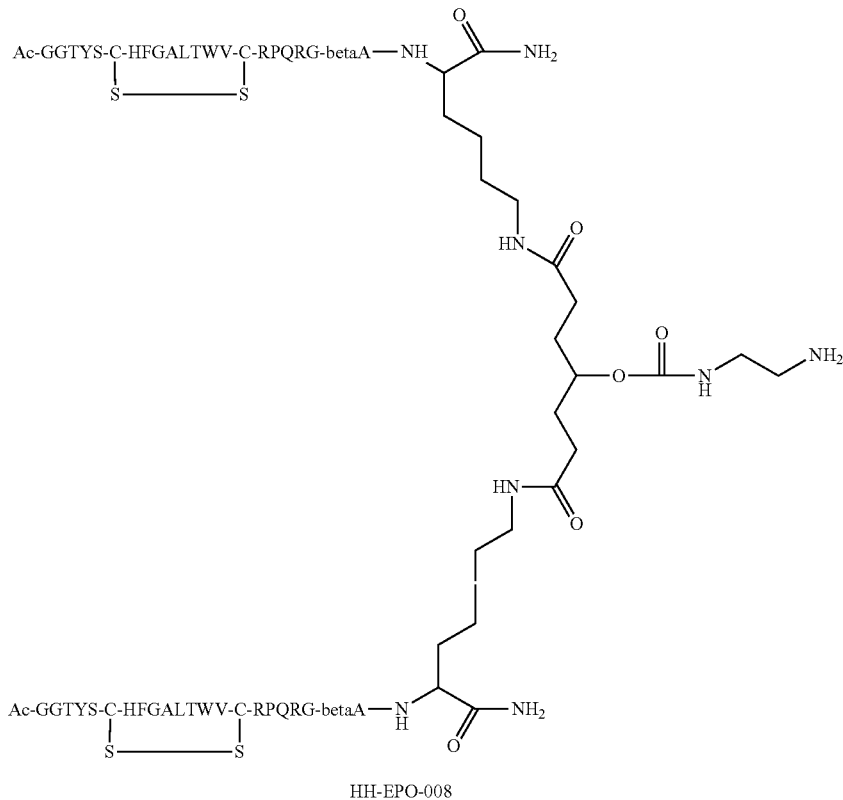

HH-EPO-008

Step 1: Preparation of SEQ ID NO: 8 Cyclic Peptide

The peptide monomer of SEQ ID NO: 8 (27 g, synthesized in accordance with the method given in the Examples) is dissolved in 3000 mL of 20% glacial acetic acid. A 5% iodine-methanol solution is added dropwise until the yellow color does not disappear. The reaction solution is directly subjected to a preparative purification by reversed-phase chromatography, using octadecylsilane bonded silica gel as column filler (Waters SymmetryShield™ RP18, 3.5 μm, 4.6*100 mm). The column temperature is 60° C. and the detection wavelength is 214 nm. Water (containing 0.05% trifluoroacetic acid) and acetonitrile (containing 0.05% trifluoroacetic acid) in different proportions are used as mobile phases. The target fractions are collected and combined. After most of the acetonitrile is distilled off under reduced pressure and the residue is freeze-dried, 9.3 g of SEQ ID NO:8 is obtained (Yield: 15.7%).

Step 2: Preparation of HH-EPO-008

The cyclic peptide of SEQ ID NO: 8 (3.0 g, 1.22 mmol) is dissolved in 150 mL of N,N-dimethyl formamide. Triethylamine (147 mg, 1.46 mmol) and the functional small molecule (LG-3) (368 mg, 0.61 mmol) are added into the solution. After the reaction is stirred at room temperature for 6 hours, part of the N,N-dimethylformamide is removed. 200 mL of ether is added into the residue. The mixture is placed in a refrigerator for 2 hours and then centrifuged. A white solid is obtained by vacuum drying. Then this white solid is dissolved in 50 mL of 20% trifluoroacetic acid in dichloromethane solution. After the mixture is stirred at room temperature for 30 minutes, part of the solvent is removed under reduced pressure. 200 mL of ether is added into the residue. The mixture is placed in the refrigerator for 2 hours and then centrifuged. A white solid is obtained and dried under vacuum. The white solid is subjected to a preparative purification by reversed-phase chromatography, using octadecylsilane bonded silica gel as column filler (Waters SymmetryShield™ RP18, 3.5 μm, 4.6*100 mm). The column temperature is 60° C. and the detection wavelength is 214 nm. Water (containing 0.05% trifluoroacetic acid) and acetonitrile (containing 0.05% trifluoroacetic acid) in different proportions are used as mobile phases. The target fractions are collected and combined. After most of the acetonitrile is distilled off under reduced pressure and the residue is freeze-dried, 1.12 g of HH-EPO-008 is obtained (Yield is about 33%).

EXAMPLE 10

Preparation of HH-EPO-008A

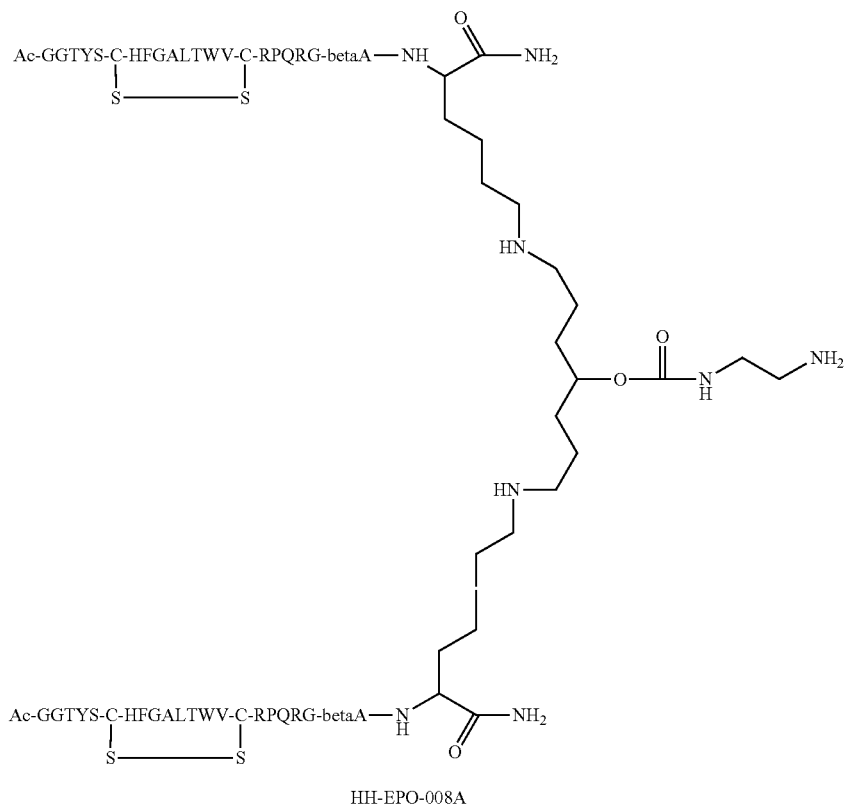

HH-EPO-008A

The cyclic peptide of SEQ ID NO: 8 (3.0 g, 1.22 mmol) is dissolved in 150 mL of 20 mmol acetic acid buffer (pH5.0). The functional small molecule (LG-4) (201 mg, 0.61 mmol) and 10 mL of acetonitrile are added into the solution. After stirred at room temperature for 30 minutes, the reaction solution is subjected a preparative purification by reversed-phase chromatography, using octadecylsilane bonded silica gel as column filler (Waters SymmetryShield™ RP18, 3.5 μm, 4.6*100 mm). The column temperature is 60° C. and the detection wavelength is 214 nm. Water (containing 0.05% trifluoroacetic acid) and acetonitrile (containing 0.05% trifluoroacetic acid) in different proportions are used as mobile phases. The target fractions are collected and combined. After most of the acetonitrile is distilled off under reduced pressure and the residue is freeze-dried, 0.75 g of HH-EPO-008A is obtained (Yield: 25%).

EXAMPLE 11

Preparation of HH-EPO-008B

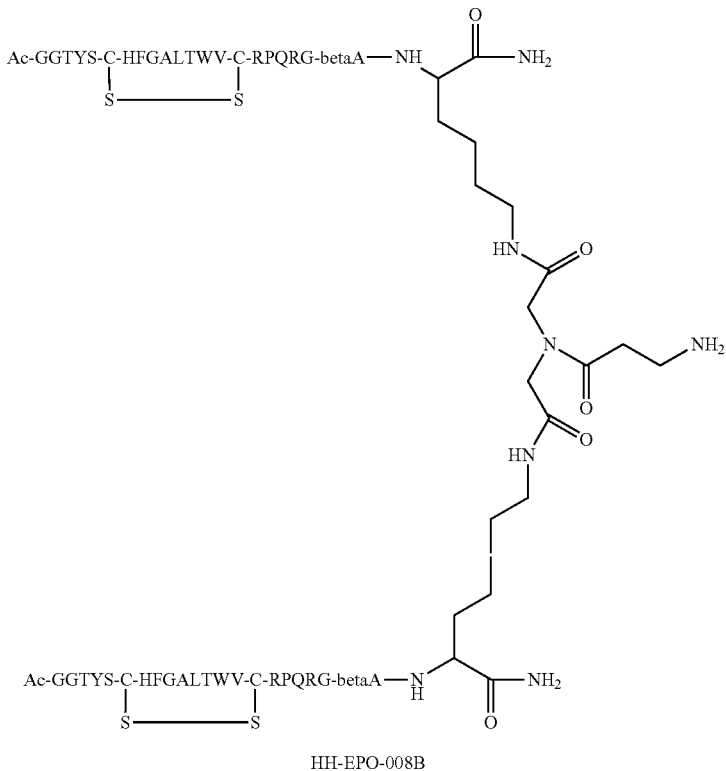

HH-EPO-008B

The cyclic peptide SEQ ID NO: 8 (3.0 g, 1.22 mmol) is dissolved in 150 mL of N,N-dimethyl formamide. Triethylamine (147 mg, 1.46 mmol) and the functional small molecule (LG-2) (322 mg, 0.61 mmol) are added into the solution. After the reaction is stirred at room temperature for 6 hours, part of the N,N-dimethylformamide is removed. 200 mL of ether is added into the residue. The mixture is placed in a refrigerator for 2 hours and then centrifuged. A white solid is obtained and dried under vacuum. Then this white solid is dissolved in 50 mL of 20% trifluoroacetic acid in dichloromethane solution. After the solution is stirred at room temperature for 30 minutes, part of the solvent is removed under reduced pressure. 200 mL of ether is added into the residue. The mixture is placed in the refrigerator for 2 hours and then centrifuged. A white solid is obtained and dried under vacuum. The white solid is subjected to a preparative purification by reversed-phase chromatography, using octadecyl silane bonded silica gel as column filler (Waters Symmetry-Shield™ RP18, 3.5 μm, 4.6*100 mm). The column temperature is 60° C. and the detection wavelength is 214 nm. Water (containing 0.05% trifluoroacetic acid) and acetonitrile (containing 0.05% trifluoroacetic acid) in different proportions are used as mobile phases. The target fractions are collected and combined. After most of the acetonitrile is distilled off under reduced pressure and the residue is freeze-dried, 1.3 g of HH-EPO-008 is obtained (Yield is about 43%).

EXAMPLE 12

Preparation of HH-EPO-008C

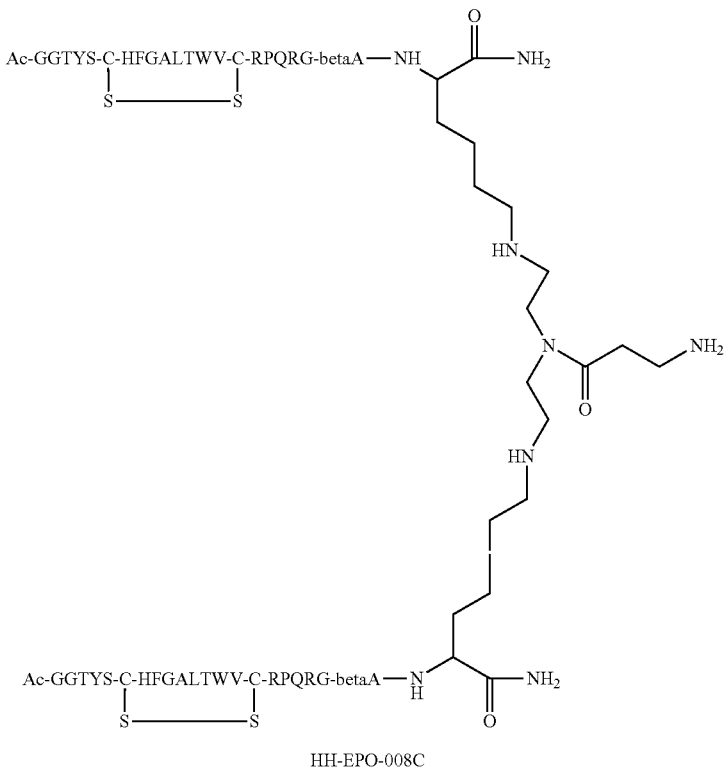

HH-EPO-008C

The cyclic peptide SEQ ID NO: 8 (3.0 g, 1.22 mmol) is dissolved in 150 mL of 20 mmol acetic acid buffer (pH5.0). Then the functional small molecule (LG-1) (165 mg, 0.61 mmol) and 10 mL of acetonitrile are added. After stirred at room temperature for 30 minutes, the reaction solution is subjected to a preparative purification by reversed-phase chromatography, using octadecylsilane bonded silica gel as column filler (Waters SymmetryShield™ RP18, 3.5 μm, 4.6*100 mm). The column temperature is 60° C. and the detection wavelength is 214 nm. Water (containing 0.05% trifluoroacetic acid) and acetonitrile (containing 0.05% trifluoroacetic acid) in different proportions are used as mobile phases. The target fractions are collected and combined. After most of the acetonitrile is distilled off under reduced pressure and the resulting residue is freeze-dried, 0.8 g of HH-EPO-008C is obtained (Yield: 27%).

EXAMPLE 13

Preparation of HH-EPO-018

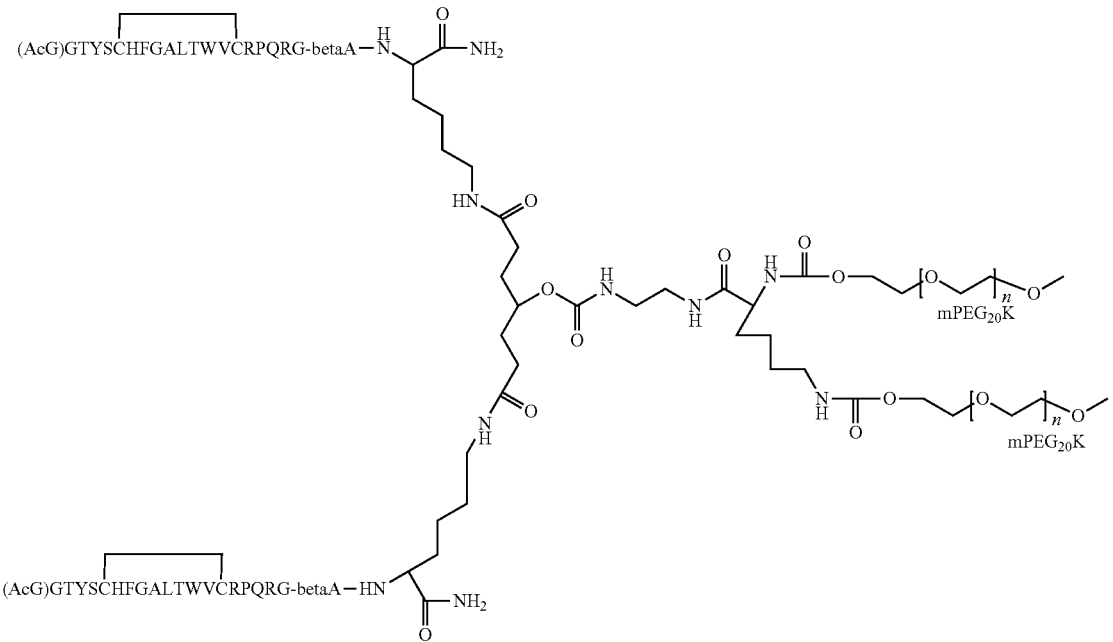

HH-EPO-008 (0.5 g, 0.98 mmol) is dissolved in 100 mL of N, N-dimethyl formamide. Triethylamine (39.6 mg, 0.196 mmol) and mPEG$_2$-OSU (40K) (3.8 g, 0.96 mmol) are added into the solution. After stirred at room temperature for 6 hours, the reaction solution is poured directly into 600 mL of cold ether. A solid is precipitated. After placing in a refrigerator for 2 hours, the mixture is centrifuged and the resulting crude HH-EPO-018 is dried under vacuum. Crude HH-EPO-018 is purified by reversed-phase chromatography, using octadecyl silane bonded silica gel as column filler (Waters SymmetryShield™ RP18, 3.5 μm, 4.6*100 mm). The column temperature is 60° C. and the detection wavelength is 214 nm. Water (containing 0.05% trifluoroacetic acid) and acetonitrile (containing 0.05% trifluoroacetic acid) in different proportions are used as mobile phases. The target fractions are collected and combined. After most of the acetonitrile is distilled off under reduced pressure and the resulting residue is freeze-dried, 1.8 g of HH-EPO-018 (Yield is about 47%).

EXAMPLE 14

Preparation of HH-EPO-018A

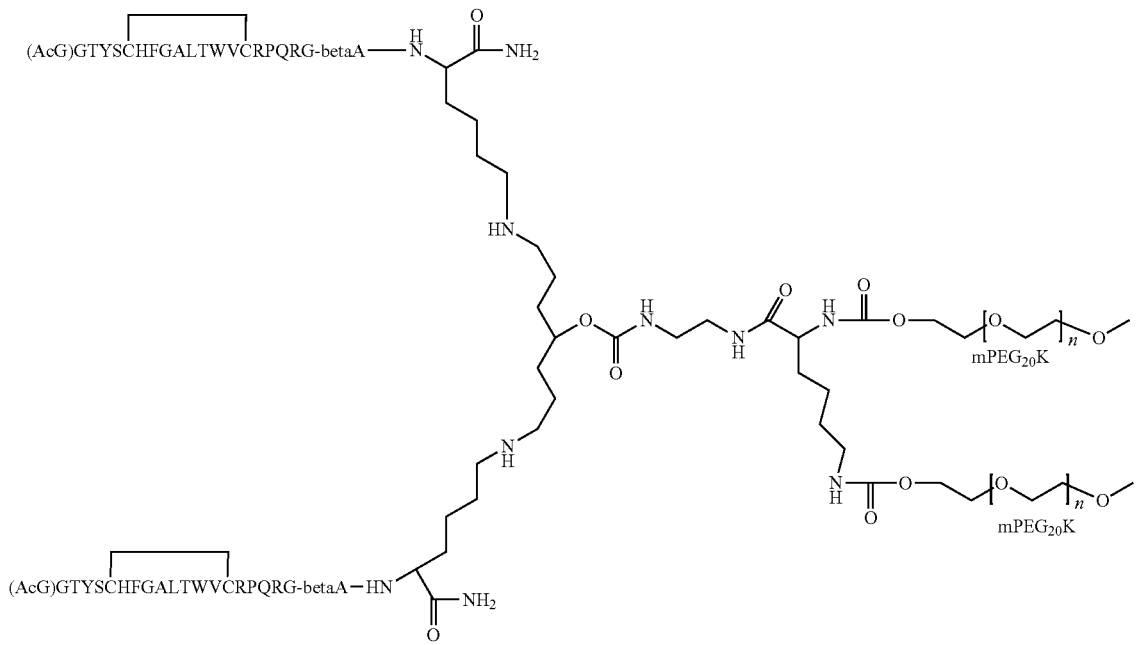

HH-EPO-008 (0.5 g, 0.98 mmol) is dissolved in 100 mL of N,N-dimethyl formamide. Triethylamine (39.6 mg, 0.196 mmol) and mPEG$_2$-OSU (40K) (3.8 g, 0.96 mmol) are added into the solution. The reaction is stirred at room temperature for 6 hours. The reaction solution is directly poured into 600 mL of cold ether. A solid is precipitated. After placing in the refrigerator for 2 hours, the mixture is centrifuged and the resulting crude HH-EPO-018 is dried under vacuum. Crude HH-EPO-018 is purified by reversed-phase chromatography, using octadecyl silane bonded silica gel as column filler (Waters SymmetryShield™ RP18, 3.5 μm, 4.6*100 mm). The column temperature is 60° C. and the detection wavelength is 214 m. Water (containing 0.05% trifluoroacetic acid) and acetonitrile (containing 0.05% trifluoroacetic acid) in different proportions are used as mobile phases. The target fractions are collected and combined. After most of the acetonitrile is distilled off under reduced pressure and the resulting residue is freeze-dried, 1.5 g of HH-EPO-018A is obtained (Yield is about 39%).

EXAMPLE 15

Preparation of HH-EPO-018B

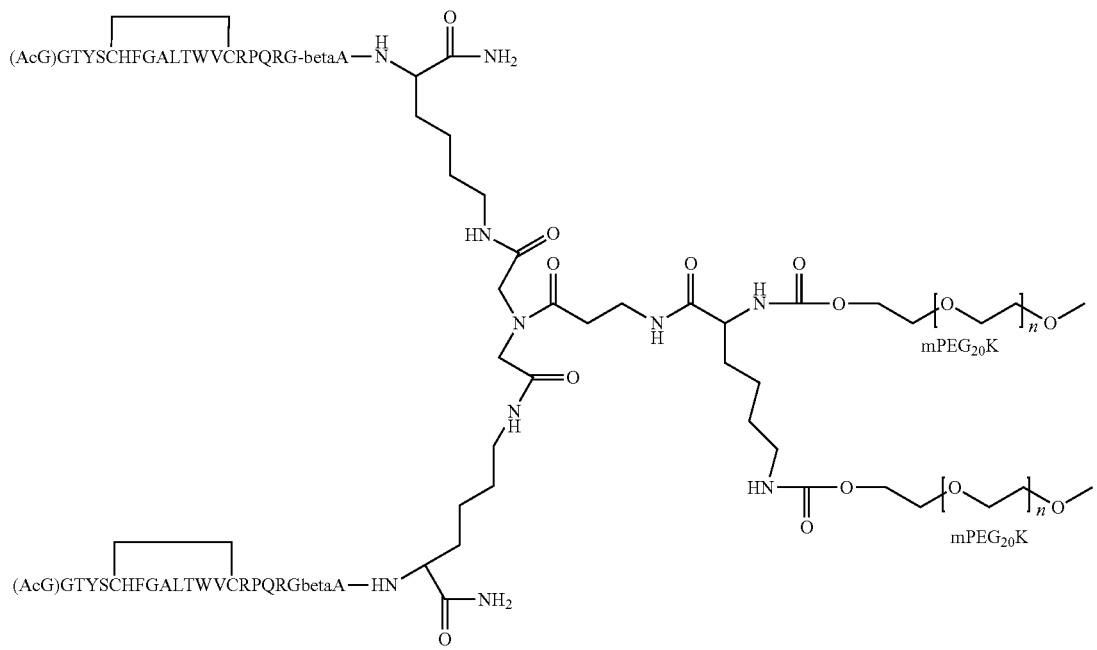

HH-EPO-008 (0.5 g, 0.98 mmol) is dissolved in 100 mL of N,N-dimethyl formamide. Triethylamine (39.6 mg, 0.196 mmol) and mPEG$_2$-OSU (40K) (3.8 g, 0.96 mmol) are added into the solution. The reaction is stirred at room temperature for 6 hours and directly poured into 600 mL of cold ether. A solid is precipitated. After placing in a refrigerator for 2 hours, the mixture is centrifuged and the resulting crude HH-EPO-018 is dried under vacuum. Crude HH-EPO-018 is purified by reversed-phase chromatography, using octadecyl silane bonded silica gel as column filler (Waters SymmetryShield™ RP18, 3.5 μm, 4.6*100 mm). The column temperature is 60° C. and the detection wavelength is 214 nm. Water (containing 0.05% trifluoroacetic acid) and acetonitrile (containing 0.05% trifluoroacetic acid) in different proportions are used as mobile phases. The target fractions are collected and combined. After most of the acetonitrile is distilled off under reduced pressure and the resulting residue is freeze-dried, 1.7 g of HH-EPO-018 is obtained (Yield is about 45%).

EXAMPLE 16

Preparation of HH-EPO-018C

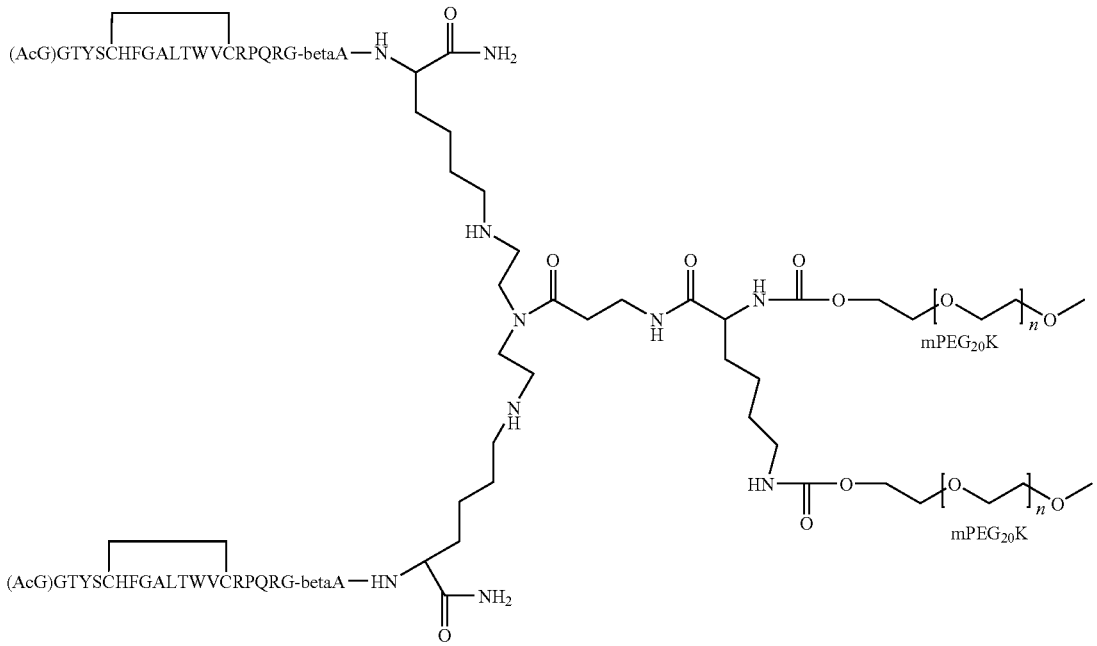

HH-EPO-008 (0.5 g, 0.98 mmol) is dissolved in 100 mL of N,N-dimethyl formamide. Triethylamine (39.6 mg, 0.196 mmol) and mPEG$_2$-OSU (40K) (3.8 g, 0.96 mmol) are added into the solution. The reaction is stirred at room temperature for 6 hours. The reaction solution is poured directly into 600 mL of cold ether. A solid is precipitated. After placing in the refrigerator 2 hours, the mixture is centrifuged and the resulting crude HH-EPO-018 is dried under vacuum. Crude HH-EPO-018 is purified by reversed-phase chromatography, using octadecylsilane bonded silica gel as column filler (Waters SymmetryShield™ RP18, 3.5 μm, 4.6*100 mm). The column temperature is 60° C. and the detection wavelength is 214 nm. Water (containing 0.05% trifluoroacetic acid) and acetonitrile (containing 0.05% trifluoroacetic acid) in different proportions are used as mobile phases. The target fractions are collected and combined. After most of the acetonitrile is distilled off under reduced pressure and the resulting residue is freeze-dried, 1.4 g of HH-EPO-018 is obtained (Yield is about 37%).

EXAMPLE 17

Effects of EPO Mimetic Peptide Derivatives on Mice
Purpose of the Experiments The purpose of the experiments is to evaluate and compare the effects of EPO mimetic peptide derivatives and the EPO protein on erythropoiesis of mice.

Materials and Method

EPO mimetic peptide derivatives including HH-EPO-001, HH-EPO-002, HH-EPO-003, HH-EPO-004, HH-EPO-005, HH-EPO-006, HH-EPO-007, HH-EPO-008, HH-EPO-015, HH-EPO-016, HH-EPO-017 and HH-EPO-018 are provided by Jiangsu Hansoh Pharmaceutical co., LTD. EPO is purchased from Shenyang Sansheng Pharmaceutical Co., Ltd.

Kunming mice are purchased from the Chinese Academy of Sciences Shanghai Experimental Animal Center, weighing 25~30 g, ♀. The number of animals in each group is 10.

Mice are injected subcutaneously with EPO mimetic peptide derivatives and EPO protein for three consecutive days. Then the mice are killed, the whole blood is used to carry out peripheral blood cells and reticulocyte counts. Blood cell count is performed using automatic blood cell counter counts.

Results and Discussion

According to the current dosage regimen, both EPO mimetic peptide derivatives and the EPO protein can significantly promote the increase of mouse peripheral blood reticulocyte count, indicating that they stimulate erythropoiesis (See Table 1). EPO mimetic peptide derivatives and the EPO protein have no significant influence on mature red blood cells, blood cell hematocrit, hemoglobin content (See Table 2), and also have no significant influence on the peripheral white blood cell count (See Table 3).

TABLE 1

Effects of EPO mimetic peptide derivatives on mouse reticulocyte erythropoiesis.

| Group | Mouse (number) | Dose and Programs | Reticulocyte Count ($\times 10^9$/L, x ± SD) |
|---|---|---|---|
| Control | 10 | 0.1% BSA in NS | 136.9 ± 5.6 |
| HH-EPO-005 | 10 | 4.5 mg/kg, sc, d1-3 | 947.2 ± 14.7 |
| HH-EPO-006 | 10 | 4.5 mg/kg, sc, d1-3 | 515.0 ± 22.7 |
| HH-EPO-007 | 10 | 4.5 mg/kg, sc, d1-3 | 553.5 ± 26.6 |
| HH-EPO-008 | 10 | 4.5 mg/kg, sc, d1-3 | 908.1 ± 21.7 |
| HH-EPO-015 | 10 | 4.5 mg/kg, sc, d1-3 | 1146.9 ± 176.6 |
| HH-EPO-016 | 10 | 4.5 mg/kg, sc, d1-3 | 1796.4 ± 304.4 |
| HH-EPO-017 | 10 | 4.5 mg/kg, sc, d1-3 | 1208.9 ± 178.5 |
| HH-EPO-018 | 10 | 4.5 mg/kg, sc, d1-3 | 2000.6 ± 272.0 |
| HH-EPO-018A | 10 | 4.5 mg/kg, sc, d1-3 | 1889.3 ± 252.0 |

TABLE 1-continued

Effects of EPO mimetic peptide derivatives on mouse reticulocyte erythropoiesis.

| Group | Mouse (number) | Dose and Programs | Reticulocyte Count ($\times 10^9$/L, x ± SD) |
|---|---|---|---|
| HH-EPO-018B | 10 | 4.5 mg/kg, sc, d1-3 | 1969.7 ± 312.0 |
| HH-EPO-018C | 10 | 4.5 mg/kg, sc, d1-3 | 1879.3 ± 162.0 |
| EPO | 10 | 5 μg/kg, sc, d1-3 | 483.9 ± 146.5 |

TABLE 2

Effects of EPO mimetic peptide derivatives on mouse erythropoiesis, blood cell hematocrit, and hemoglobin content.

| Group | Mouse (number) | Dose and Programs | Red Blood Cell Count ($\times 10^6$/μL, x ± SD) | Blood Cell Hematocrit (%) | Hemoglobin (%) |
|---|---|---|---|---|---|
| Control | 10 | 0.1% BSA in NS | 9.6 ± 0.5 | 48.2 ± 3.0 | 14.8 ± 0.7 |
| HH-EPO-005 | 10 | 4.5 mg/kg, sc, d1-3 | 10.1 ± 0.6 | 54.4 ± 3.2 | 16.3 ± 0.9 |
| HH-EPO-006 | 10 | 4.5 mg/kg, sc, d1-3 | 9.6 ± 0.5 | 50.5 ± 2.8 | 15.3 ± 0.9 |
| HH-EPO-007 | 10 | 4.5 mg/kg, sc, d1-3 | 9.1 ± 3.1 | 49.4 ± 17.1 | 14.8 ± 4.8 |
| HH-EPO-008 | 10 | 4.5 mg/kg, sc, d1-3 | 9.6 ± 0.2 | 54.0 ± 1.7 | 16.1 ± 0.5 |
| HH-EPO-015 | 10 | 4.5 mg/kg, sc, d1-3 | 10.0 ± 0.40 | 54.57 ± 2.50 | 15.01 ± 0.57 |
| HH-EPO-016 | 10 | 4.5 mg/kg, sc, d1-3 | 9.88 ± 0.42 | 56.50 ± 2.95 | 13.24 ± 4.2 |
| HH-EPO-017 | 10 | 4.5 mg/kg, sc, d1-3 | 9.70 ± 0.30 | 55.84 ± 2.33 | 14.93 ± 0.55 |
| HH-EPO-018 | 10 | 4.5 mg/kg, sc, d1-3 | 9.69 ± 0.33 | 56.97 ± 3.13 | 13.22 ± 2.66 |
| HH-EPO-018A | 10 | 4.5 mg/kg, sc, d1-3 | 9.44 ± 0.65 | 54.47 ± 2.61 | 14.35 ± 1.35 |
| HH-EPO-018B | 10 | 4.5 mg/kg, sc, d1-3 | 9.77 ± 0.51 | 55.71 ± 3.31 | 13.72 ± 2.35 |
| HH-EPO-018C | 10 | 4.5 mg/kg, sc, d1-3 | 9.59 ± 0.53 | 54.98 ± 2.83 | 13.86 ± 2.47 |
| EPO | 10 | 5 μg/kg, sc, d1-3 | 9.0 ± 0.6 | 46.2 ± 2.7 | 14.3 ± 0.7 |

TABLE 3

Effects of EPO mimetic peptide derivatives on mouse platelets and white blood cell generation.

| Group | Mouse (number) | Dose and Programs | Platelet ($\times 10^3$/μL) | White Blood Cell ($\times 10^3$/μL) |
|---|---|---|---|---|
| Control | 10 | 0.1% BSA in NS | 1078.0 ± 151.2 | 5.1 ± 1.5 |
| HH-EPO-005 | 10 | 4.5 mg/kg, sc, d1-3 | 1957.8 ± 349.5 | 4.2 ± 1.2 |
| HH-EPO-006 | 10 | 4.5 mg/kg, sc, d1-3 | 1087.8 ± 118.5 | 4.1 ± 1.2 |
| HH-EPO-007 | 10 | 4.5 mg/kg, sc, d1-3 | 2082.1 ± 863.9 | 3.6 ± 0.8 |
| HH-EPO-008 | 10 | 4.5 mg/kg, sc, d1-3 | 1685.5 ± 351.3 | 2.9 ± 0.5 |
| HH-EPO-015 | 10 | 4.5 mg/kg, sc, d1-3 | 1106.6 ± 170.03 | 4.32 ± 1.29 |
| HH-EPO-016 | 10 | 4.5 mg/kg, sc, d1-3 | 1275.88 ± 239.90 | 5.06 ± 1.41 |
| HH-EPO-017 | 10 | 4.5 mg/kg, sc, d1-3 | 1109.60 ± 130.73 | 4.25 ± 1.65 |
| HH-EPO-018 | 10 | 4.5 mg/kg, sc, d1-3 | 1317.50 ± 461.06 | 4.11 ± 1.31 |
| HH-EPO-018A | 10 | 4.5 mg/kg, sc, d1-3 | 1432.50 ± 453.05 | 4.23 ± 1.23 |
| HH-EPO-018B | 10 | 4.5 mg/kg, sc, d1-3 | 1337.70 ± 363.06 | 4.07 ± 1.23 |
| HH-EPO-018C | 10 | 4.5 mg/kg, sc, d1-3 | 1355.50 ± 331.07 | 4.21 ± 1.34 |
| EPO | 10 | 5 μg/kg, sc, d1-3 | 1306.8 ± 170. | 4.0 ± 0.9 |

EXAMPLE 18

Effects of EPO Mimetic Peptide Derivatives on Macaques Purpose of this Experiment The purpose of this experiment is to evaluate the effects of EPO mimetic peptide derivatives on erythropoiesis of the macaques.

Materials and Methods

EPO mimetic peptide HH-EPO-018 is provided by Jiangsu Hansoh Pharmaceutical co., LTD. EPO is purchased from Shenyang Sansheng Pharmaceutical Co., Ltd. The samples are diluted in a saline containing 0.1% BSA before they are used.

Macaques, weighing 5.5~8.5 kg, male or female, are purchased from Suzhou Xishan Zhongke Laboratory Animal Center. Macaques are grouped according to the basis of hemoglobin with each group having three macaques. HH-EPO-018 is intravenously injected once at a dose of 1.35 mg/kg; EPO is injected three times per week at a dose of 240 μg/kg. The administration is continued for five weeks. Measure hematological indexes are measured 1~2 times per week.

Results and Discussion

Figure 2:
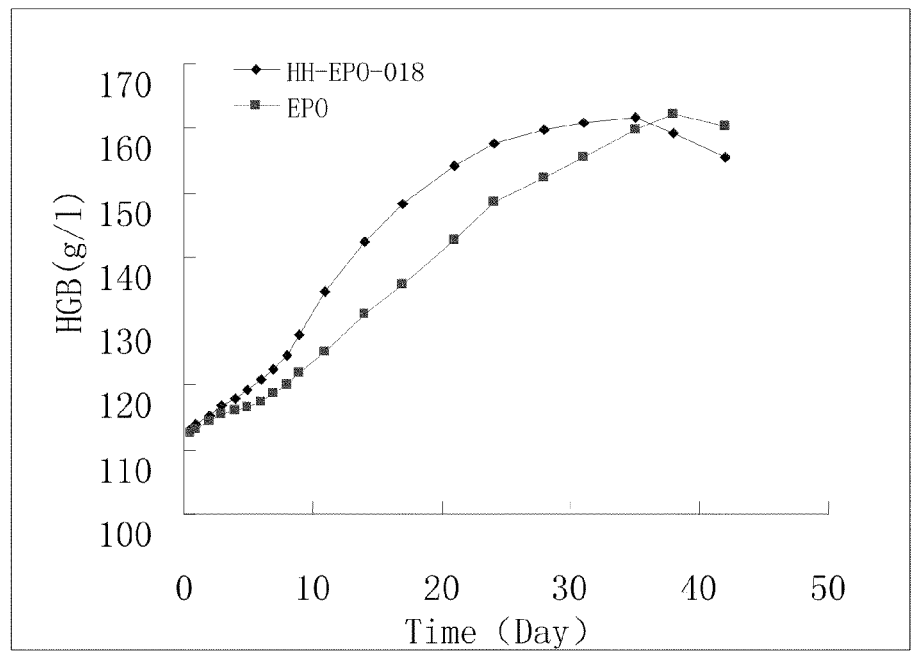
FIG. 2 shows the influence of EPO mimetic peptide derivatives (HH-EPO-018) on hemoglobin of macaques.

Single intravenous injection of HH-EPO-018 on macaques leads to an increase of peripheral blood hemoglobin, and an increase of blood cell hematocrit, indicating that HH-EPO-018 stimulate erythropoiesis. The stimulation peaks at 35 days after the administration, and then decreases slowly. The stimulatory effect of hemoglobin is about 33%. As a positive control, EPO also increases the peripheral blood hemoglobin content and blood cell hematocrit of macaque. The effect declines slowly after the administering is stopped. According to the current dosing regimens, the stimulation of HH-EPO-018 and EPO on macaque hemoglobin generation is similar (see FIGS. 1 and 2).

EXAMPLE 19

To Evaluate and Compare the Effects of EPO Mimetic Peptide Derivatives HH-EPO-015, HH-EPO-018, HH-EPO-018B and Positive Control AF37702 on the Mice Materials and Methods HH-EPO-015, HH-EPO-018, and HH-EPO-018B, are provided by Jiangsu Hansoh Pharmaceutical co., LTD. AF37702 is also EPO mimetic peptide derivative, produced by Affymax (brand name: Hematide). The samples are diluted in a saline containing 0.1% BSA. Kunming mice are purchased from the Chinese Academy of Sciences Shanghai Experimental Animal Center, weighing 25~30 g, ♀. The number of animals in each group is 10. After adaptation, animals are subcutaneously injected with HH-EPO-015, HH-EPO-018, HH-EPO-018B, and AF37702, respectively. The mice are scarified on the sixth day after the first dose. The whole blood is used to carry out peripheral blood cells and reticulocyte count. Blood cell count is performed using an ADVIA automatic blood cell counter.

Results and Discussion

A single subcutaneous injection of HH-EPO-015, HH-EPO-018, HH-EPO-018B, and AF37702 all elevate the mouse peripheral blood reticulocyte percentage and counts. The effects of HH-EPO-018B is relatively strong; the effects of HH-EPO-018 and AF37702 follow; the effects of HH-EPO-015 is the weakest; and the effects of HH-EPO-018 and AF37702 are roughly equal (see Table 4). HH-EPO-015, HH-EPO-018, HH-EPO-018B and AF37702 elevate the mouse peripheral blood cell hematocrit, hemoglobin content. Their effects are roughly equal, but they all have no significant influence on the peripheral red blood cell count (See Table 5).

TABLE 4

Effects of HH-EPO-015, HH-EPO-018, HH-EPO-018B and AF37702 on the mouse peripheral blood reticulocyte erythropoiesis.

| Group | Mouse (number) | Dose and Program | Reticulocyte Erythropoiesis (x ± SD) | Reticulocyte Erythropoiesis Counting ($\times 10^9$/L, x ± SD) |
| --- | --- | --- | --- | --- |
| Control | 10 | 0.1% BSA in NS | 2.8 ± 1.0 | 195.0 ± 73.1 |
| HH-EPO-015 | 10 | 2.5 mg/kg, sc, d1 | 6.9 ± 2.1** | 511.9 ± 191.7** |
| HH-EPO-015 | 10 | 5.0 mg/kg, sc, d1 | 8.9 ± 2.4** | 558.9 ± 230.5** |
| HH-EPO-018 | 10 | 2.5 mg/kg, sc, d1 | 16.2 ± 3.5** | 1137.3 ± 240.2** |
| HH-EPO-018 | 10 | 5.0 mg/kg, sc, d1 | 16.0 ± 3.2** | 1113.2 ± 210.7** |
| HH-EPO-018B | 10 | 2.5 mg/kg, sc, d1 | 19.0 ± 8.9** | 1336.5 ± 629.0** |
| HH-EPO-018B | 10 | 5.0 mg/kg, sc, d1 | 20.0 ± 5.3** | 1440.3 ± 416.5** |
| AF37702 | 10 | 2.5 mg/kg, sc, d1 | 13.5 ± 4.1** | 865.2 ± 291.4** |
| AF37702 | 10 | 5.0 mg/kg, sc, d1 | 17.2 ± 5.3** | 1202.8 ± 355.4** |

**$P < 0.01$ vs control

TABLE 5

Effects of HH-EPO-015, HH-EPO-018, HH-EPO-018B and AF37702 on mouse peripheral erythropoiesis, blood cell hematocrit, and hemoglobin content.

| Group | Mouse (number) | Dose and Programs | Red Blood Cell Count ($\times 10^6$/uL, x ± SD) | Blood Cell Hematocrit ($\times 10^9$/L, x ± SD) | Hemoglobin (g/dL) |
| --- | --- | --- | --- | --- | --- |
| Control | 10 | 0.1% BSA in NS | 6.9 ± 0.5 | 38.6 ± 2.8 | 12.5 ± 0.9 |
| HH-EPO-015 | 10 | 2.5 mg/kg, sc, d1 | 7.5 ± 0.3 | 42.7 ± 1.8* | 14.3 ± 0.6** |
| HH-EPO-015 | 10 | 5.0 mg/kg, sc, d1 | 6.3 ± 1.7 | 36.5 ± 9.9 | 13.1 ± 4.5 |
| HH-EPO-018 | 10 | 2.5 mg/kg, sc, d1 | 7.0 ± 0.3 | 40.6 ± 1.6 | 13.3 ± 2.2 |
| HH-EPO-018 | 10 | 5.0 mg/kg, sc, d1 | 7.0 ± 0.3 | 41.5 ± 1.2* | 14.2 ± 0.8** |
| HH-EPO-018B | 10 | 2.5 mg/kg, sc, d1 | 6.6 ± 1.4 | 39.0 ± 7.7 | 14.2 ± 0.6** |
| HH-EPO-018B | 10 | 5.0 mg/kg, sc, d1 | 7.0 ± 0.4 | 41.6 ± 2.6* | 14.4 ± 0.9** |
| AF37702 | 10 | 2.5 mg/kg, sc, d1 | 7.1 ± 0.4 | 41.9 ± 3.1* | 14.1 ± 1.1** |
| AF37702 | 10 | 5.0 mg/kg, sc, d1 | 7.2 ± 0.3 | 42.5 ± 3.4* | 14.0 ± 0.8** |

*$P < 0.05$,
**$P < 0.01$ vs control

What is claimed is:

1. A peptide mimetic of formula (I):

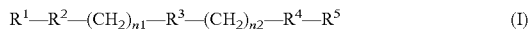

$$R^1-R^2-(CH_2)_{n1}-R^3-(CH_2)_{n2}-R^4-R^5 \quad (I)$$

or a pharmaceutically acceptable salt thereof, wherein:
$R^1$ and $R^5$ are independently selected from an amino acid sequence selected from SEQ ID Nos: 1-30;
n1 and n2 are integers independently selected from 0-10;
$R^2$ and $R^4$ are independently selected from the group consisting of —CO— and —CH$_2$—; and
$R^3$ is selected from the group consisting of O, S, CH$_2$, N(CH$_2$)$_{n3}$NHR$^6$, NCO(CH$_2$)$_{n4}$NHR$^6$, CHOCONH(CH$_2$)$_{n5}$NHR$^6$, CHSCON(CH$_2$)$_{n5}$NHR$^6$, and CHNHCON(CH$_2$)$_{n5}$NHR$^6$;
wherein n3 is an integer selected from 1-10, n4 is an integer selected from 2-10, n5 is an integer selected from 2-10; and R$^6$ is selected from the group consisting of hydrogen and methoxy polyethylene glycol derivatives.

2. The peptide mimetic of claim 1, or a pharmaceutically acceptable salt thereof, wherein R$^1$ and R$^5$ independently comprise an amino acid sequence selected from SEQ ID Nos: 1-8.

3. The peptide mimetic of claim 2, or a pharmaceutically acceptable salt thereof, wherein R$^1$ and R$^5$ independently comprise SEQ ID No: 8.

4. The peptide mimetic of claim 1, or a pharmaceutically acceptable salt thereof, wherein R$^1$ and R$^5$ comprise the identical amino acid sequence.

5. The peptide mimetic of claim 1, or a pharmaceutically acceptable salt thereof; wherein R$^1$ and R$^5$ comprise different amino acid sequences.

6. The peptide mimetic of claim 1, or a pharmaceutically acceptable salt thereof, wherein the N-terminals of R$^1$ and R$^5$ are acetylated.

7. The peptide mimetic of claim 1, or a pharmaceutically acceptable salt thereof, wherein at least one of R$^1$ and R$^5$ is a cyclic peptide.

8. The peptide mimetic of claim 7, or a pharmaceutically acceptable salt thereof, wherein at least one of R$^1$ and R$^5$ contains an intramolecular disulfide bond.

9. The peptide mimetic of claim 1, or a pharmaceutically acceptable salt thereof, wherein R$^1$ and R$^5$ independently comprise an amino acid sequence with a length of 13 to 40 amino acids.

10. The peptide mimetic of claim 9, or a pharmaceutically acceptable salt thereof, wherein the length is 22 amino acids.

11. The peptide mimetic of claim 1, or a pharmaceutically acceptable salt thereof, wherein n1 and n2 are 2, R$^2$ and R$^4$ are —CO, and R$_3$ is CHOCONH(CH$_2$)$_2$NHR$^6$.

12. The peptide mimetic of claim 1, or a pharmaceutically acceptable salt thereof, wherein n1 and n2 are 2, R$^2$ and R$^4$ are —CH$_2$, and R$_3$ is CHOCONH(CH$_2$)$_2$NHR$^6$.

13. The peptide mimetic of claim 1, or a pharmaceutically acceptable salt thereof, wherein n1 and n2 are 1, R$^2$ and R$^4$ are —CO, and R$_3$ is NCO(CH$_2$)$_2$NHR$^6$.

14. The peptide mimetic of claim 1, or a pharmaceutically acceptable salt thereof, wherein n1 and n2 are 1, R$^2$ and R$^4$ are —CH$_2$, and R$_3$ is NCO(CH$_2$)$_2$NHR$^6$.

15. The peptide mimetic of claim 1, or a pharmaceutically acceptable salt thereof, wherein R$^6$ is hydrogen.

16. The peptide mimetic of claim 1, or a pharmaceutically acceptable salt thereof, wherein R$^6$ is a methoxy polyethylene glycol derivative.

17. The peptide mimetic of claim 16, or a pharmaceutically acceptable salt thereof, wherein the methoxy polyethylene glycol derivative has a molecular weight of from about 5,000 to about 100,000 daltons.

18. The peptide mimetic of claim 17, or a pharmaceutically acceptable salt thereof, wherein the molecular weight of the methoxy polyethylene glycol derivative is about 20,000 daltons.

19. The peptide mimetic of claim 17, or a pharmaceutically acceptable salt thereof, wherein the molecular weight of the methoxy polyethylene glycol derivative is about 40,000 daltons.

20. The peptide mimetic of claim 16, or a pharmaceutically acceptable salt thereof, wherein the methoxy polyethylene glycol derivative is linear.

21. The peptide mimetic of claim 16, or a pharmaceutically acceptable salt thereof, wherein the methoxy polyethylene glycol derivative is branched.

22. The peptide mimetic of claim 1, or a pharmaceutically acceptable salt thereof, wherein:
n1 and n2 are 2;
$R^1$ and $R^5$ are independently selected from SEQ ID NOs: 1-8;
$R^2$ and $R^4$ are independently selected from —CO and —CH$_2$; and
$R^3$ is CHOCONH(CH$_2$)$_{n5}$NHR$^6$, wherein:
n5 is an integer selected from 2-10; and
$R^6$ is a methoxy polyethylene glycol derivative.

23. The peptide mimetic of claim 1, or a pharmaceutically acceptable salt thereof, wherein:
n1 and n2 are 1;
$R^1$ and $R^5$ are independently selected from SEQ ID NOs: 1-8;
$R^2$ and $R^4$ are independently selected from —CO and —CH$_2$; and
$R^3$ is selected from NCO(CH$_2$)$_{n4}$NHR$^6$, wherein:
n4 is an integer selected from 2-10; and
$R^6$ is a methoxy polyethylene glycol derivative.

24. A peptide mimetic of formula (I):

$$R^1—R^2—(CH_2)_{n1}—R^3—(CH_2)_{n2}—R^4—R^5 \quad (I)$$

or a pharmaceutically acceptable salt thereof; wherein:
$R^1$ and $R^5$ are independently selected from a peptide of formula: $Y^1X^1X^2X^3GX^4X^5TWX^6X^7Y^2Y^3$, wherein:
G, T, and W are glycine, threonine, and tryptophan, respectively;
$X^2$, $X^3$, $X^4$, $X^5$, $X^6$, $Y^3$ are independently selected from the group consisting of 20 genetically coded L-amino acids and non-natural amino acids;
$Y^1$ and $Y^2$ are independently selected from the group consisting of 20 genetically coded L-amino acids, non-natural amino acids, and peptide fragments comprising thereof; and
$X^1$ and $X^7$ are amino acids that can form an intramolecular bond with each other
n1 and n2 are integers independently selected from 0-10;
$R^2$ and $R^4$ are independently selected from the group consisting of —CO— and —CH$_2$—;
$R^3$ is selected from the group consisting of O, S, CH$_2$, (CH$_2$)$_{n3}$NHR$^6$, NCO(CH$_2$)$_{n4}$NHR$^6$, CHOCONH(CH$_2$)$_{n5}$NHR$^6$, CHSCON(CH$_2$)$_{n5}$NHR$^6$, CHNHCON(CH$_2$)$_{n5}$NHR$^6$,
wherein n3 is an integer selected from 1-10,
n4 is an integer selected from 2-10,
n5 is an integer selected from 2-10; and
$R^6$ is selected from the group consisting of hydrogen and methoxy polyethylene glycol derivatives.

25. The peptide mimetic of claim 24, wherein the $X^1$ and $X^7$ are independently selected from the group consisting of cysteine, lysine, aspartic acid, glutamic acid, ornithine, and homocysteine.

26. The peptide mimetic of claim 24, or a pharmaceutically acceptable salt thereof, wherein $Y^3$ is independently selected from the group consisting of lysine, histidine, and arginine.

27. The peptide mimetic of claim 26, or a pharmaceutically acceptable salt thereof, wherein $Y^3$ is lysine.

28. A peptide mimetic, or a pharmaceutically acceptable salt thereof, selected from the group consisting of:

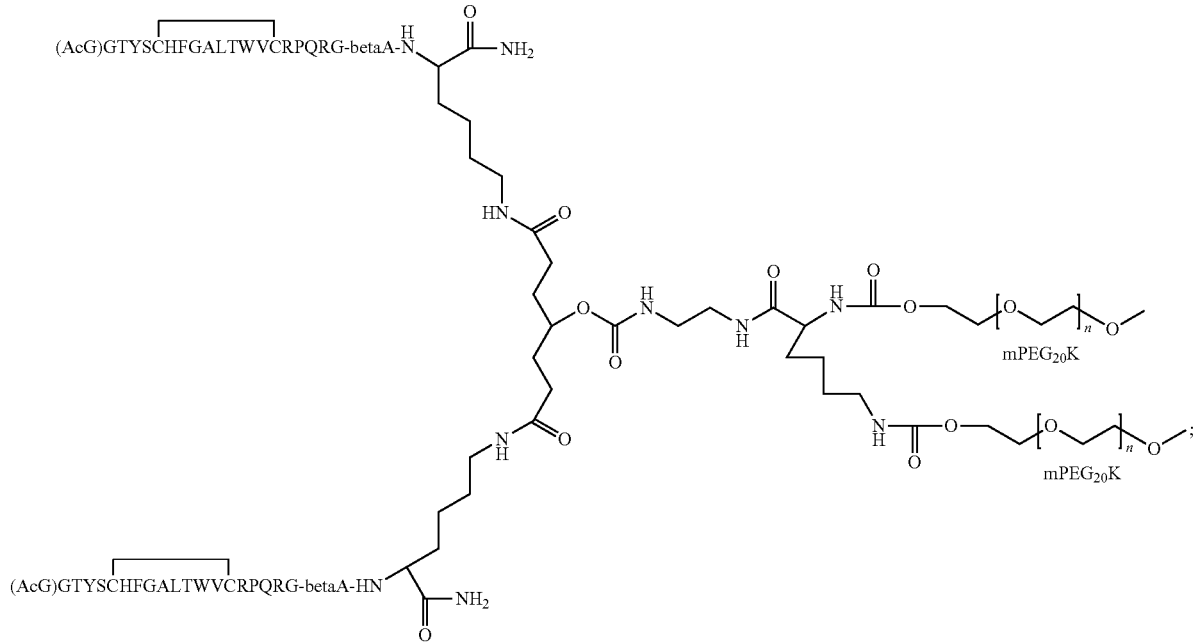

-continued
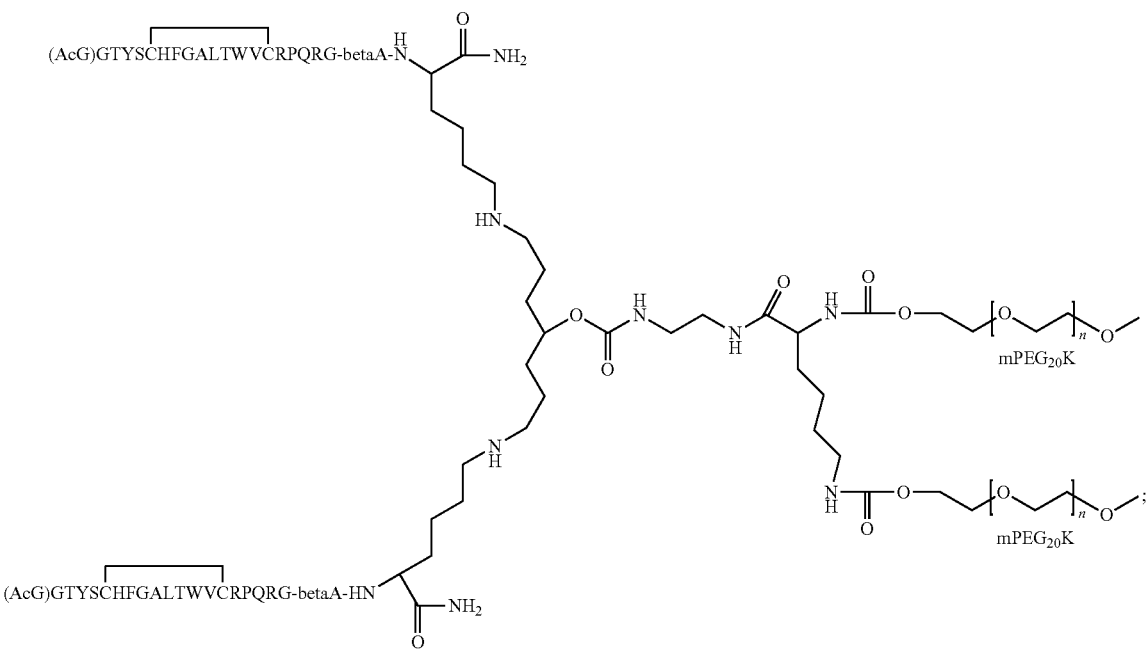
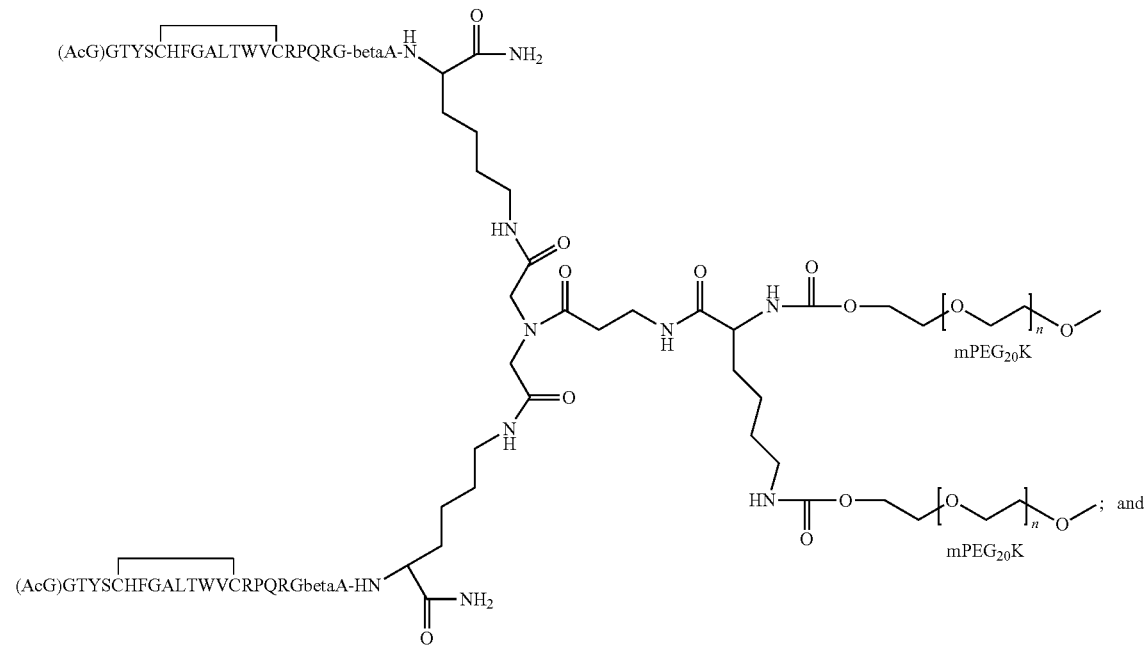

-continued

[Chemical structure showing:
(AcG)GTYSCHFGALTWVCRPQRG-betaA-N(H)—C(=O)—NH2 linked via lysine side chain through HN—CH2CH2—N—CH2CH2—NH branching to a second (AcG)GTYSCHFGALTWVCRPQRG-betaA-HN—C(=O)—NH2, with the central nitrogen attached via —C(=O)—CH2CH2—NH—C(=O)— to a lysine bearing two mPEG20K groups attached through carbamate linkages —NH—C(=O)—O—CH2CH2—(OCH2CH2)n—OCH3]

wherein:
in each peptide, each amino acid is indicated by standard one letter abbreviation, AcG is N-acetylglycine;
each peptide contains an intramolecular disulfide bond between the two cysteine (C) residues; and
mPEG 20k is a methoxy polyethylene glycol moiety having an average molecular weight of about 20,000 daltons.

29. A process for preparing a peptide mimetic, comprising:
preparing $R^1$ and $R^5$, wherein $R^1$ and $R^5$ are independently selected from an amino acid sequence selected from SEQ ID Nos: 1-30;
preparing a compound of formula (II):

$$R^7\text{—CO—}(CH_2)_{n1}\text{—}Z^2\text{—}(CH_2)_{n2}\text{—CO—}R^8 \quad (II)$$

wherein:
n1 and n2 are integers independently selected from 0 to 10;
$R^7$ and $R^8$ are selected from —OH and hydrogen; and
$Z^2$ is selected from the group consisting of O, S, $CH_2$, $N(CH_2)_{n6}NHR^9$, $NCO(CH_2)_{n7}NHR^9$, $CHOCONH(CH_2)_{n8}NHR^9$, $CHSCON(CH_2)_{n8}NHR^9$, and $CHNHCON(CH_2)_{n8}NHR^9$, wherein:
n6 is an integer selected from 1-10;
n7 is an integer selected from 2-10;
n8 is an integer selected from 2-10; and
$R^9$ is selected from tert-butyloxycarbonyl (Boc) group and carbobenzyloxy (Cbz) group;
reacting $R^1$ and $R^5$ with the compound of formula (II) to provide a compound of formula (III):

$$R^1\text{—}R^2\text{—}(CH_2)_{n1}\text{—}Z_2\text{—}(CH_2)_{n2}\text{—}R^4\text{—}R^5 \quad (III)$$

wherein $R^2$ and $R^4$ are independently selected from —CO and —$CH_2$; and
reacting the compound of formula (III) with a methoxy polyethylene glycol to provide a peptide mimetic.

30. The process of claim 29, further comprising a step of removing the group of Boc or Cbz when the compound of formula (II) comprises $R^9$.

31. The process of claim 29, wherein
n1 and n2 are independently selected from 1 and 2;
$R^7$ and $R^8$ are OH; and
$Z^2$ is selected from the group consisting of $NCO(CH_2)_{n7}NHR^9$ and $CHOCONH(CH_2)_{n8}NHR^9$; wherein
n7 is an integer selected from 2-10;
n8 is an integer selected from 2-10; and
$R^9$ is tert-butyloxycarbonyl (Boc) group.

32. The process of claim 29, wherein
n1 and n2 are independently selected from 1 and 2;
$R^7$ and $R^8$ are hydrogen; and
$Z^2$ is selected from the group consisting of $NCO(CH_2)_{n7}NHR^9$ and $CHOCONH(CH_2)_{n8}NHR^9$; wherein
n7 is an integer selected from 2-10;
n8 is an integer selected from 2-10; and
$R^9$ is tert-butyloxycarbonyl (Boc) group.

33. A pharmaceutical composition comprising the peptide mimetic of claim 1, or a pharmaceutically acceptable salt thereof, and a pharmaceutically acceptable carrier.

34. A method for treatment of disorders characterized by a low level of EPO or insufficient or defective red blood cell population, comprising administering to a patient a therapeutically effective amount of the composition of claim 33, wherein the disorder is selected from the group consisting of: end stage renal failure or dialysis; anemia associated with AIDS, autoimmune diseases, or malignant tumor; cystic fibrosis; early anemia of prematurity; chronic inflammatory disease-related anemia; spinal cord injury; acute blood loss; and erythropoiesis associated with cancer.

* * * * *

UNITED STATES PATENT AND TRADEMARK OFFICE
CERTIFICATE OF CORRECTION

| | | |
|---|---|---|
| PATENT NO. | : 8,642,545 B2 | Page 1 of 1 |
| APPLICATION NO. | : 12/747818 | |
| DATED | : February 4, 2014 | |
| INVENTOR(S) | : Lu et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 381 days.

Signed and Sealed this
Second Day of June, 2015

Michelle K. Lee
*Director of the United States Patent and Trademark Office*